United States Patent
Addison et al.

(10) Patent No.: US 10,398,353 B2
(45) Date of Patent: Sep. 3, 2019

(54) SYSTEMS AND METHODS FOR VIDEO-BASED MONITORING OF VITAL SIGNS

(71) Applicant: COVIDIEN LP, Mansfield, MA (US)

(72) Inventors: Paul Stanley Addison, Edinburgh (GB); David Foo, Glasgow (GB); Dominique Jacquel, Edinburgh (GB)

(73) Assignee: Covidien LP, Boulder, CO (US)

( * ) Notice: Subject to any disclaimer, the term of this patent is extended or adjusted under 35 U.S.C. 154(b) by 259 days.

(21) Appl. No.: 15/432,063

(22) Filed: Feb. 14, 2017

(65) Prior Publication Data
US 2017/0238805 A1  Aug. 24, 2017

Related U.S. Application Data

(60) Provisional application No. 62/297,682, filed on Feb. 19, 2016, provisional application No. 62/335,862, (Continued)

(51) Int. Cl.
*A61B 5/00* (2006.01)
*A61B 5/103* (2006.01)
(Continued)

(52) U.S. Cl.
CPC .......... *A61B 5/1032* (2013.01); *A61B 5/0077* (2013.01); *A61B 5/0205* (2013.01); *A61B 5/02416* (2013.01); *A61B 5/1176* (2013.01); *A61B 5/14542* (2013.01); *A61B 5/14551* (2013.01); *A61B 5/441* (2013.01); *A61B 5/6843* (2013.01); *A61B 5/7203* (2013.01); *A61B 5/7221* (2013.01); *A61B 5/7278* (2013.01); *A61B 5/743* (2013.01); *A61B 5/746* (2013.01); *A61B 5/748* (2013.01); *A61B 5/7425* (2013.01);
(Continued)

(58) Field of Classification Search
USPC ........................................................ 382/128
See application file for complete search history.

(56) References Cited

U.S. PATENT DOCUMENTS 5,107,845 A  4/1992  Guern et al.
5,408,998 A  4/1995  Mersch
(Continued)

FOREIGN PATENT DOCUMENTS

DE  19741982 A1  10/1998
EP  2772828  9/2014
(Continued)

OTHER PUBLICATIONS

Goldman, L. J., "Nasal airflow and thoracoabdominal motion in children using infrared thermographic video processing," Pediatric Pulmonology, vol. 47, No. 5, pp. 476-486, 2012.
(Continued)

*Primary Examiner* — Jerome Grant, II

(57) ABSTRACT

The present invention relates to the field of medical monitoring, and in particular non-contact, video-based monitoring of pulse rate, respiration rate, motion, and oxygen saturation. Systems and methods are described for capturing images of a patient, producing intensity signals from the images, filtering those signals to focus on a physiologic component, and measuring a vital sign from the filtered signals.

22 Claims, 24 Drawing Sheets

Related U.S. Application Data filed on May 13, 2016, provisional application No. 62/399,741, filed on Sep. 26, 2016.

(51) Int. Cl.
| | |
|---|---|
| *A61B 5/024* | (2006.01) |
| *A61B 5/1171* | (2016.01) |
| *A61B 5/1455* | (2006.01) |
| *A61B 5/0205* | (2006.01) |
| *A61B 5/145* | (2006.01) |
| *A61B 5/08* | (2006.01) |

(52) U.S. Cl.
CPC ............ *A61B 5/7485* (2013.01); *A61B 5/024* (2013.01); *A61B 5/0816* (2013.01); *A61B 2562/0233* (2013.01); *A61B 2576/00* (2013.01)

(56) References Cited

U.S. PATENT DOCUMENTS

| | | | |
|---|---|---|---|
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,920,236 | B2 | 7/2005 | Prokoski |
| 7,431,700 | B2 | 10/2008 | Aoki et al. |
| 8,149,273 | B2 | 4/2012 | Liu et al. |
| 8,754,772 | B2 | 6/2014 | Horng et al. |
| 8,792,969 | B2 | 7/2014 | Bernal et al. |
| 8,971,985 | B2 | 3/2015 | Bernal et al. |
| 9,226,691 | B2 | 1/2016 | Bernal et al. |
| 9,301,710 | B2 | 4/2016 | Mestha et al. |
| 9,436,984 | B2 | 9/2016 | Xu et al. |
| 9,443,289 | B2 | 9/2016 | Xu et al. |
| 9,504,426 | B2 | 11/2016 | Kyal et al. |
| 9,693,710 | B2 | 7/2017 | Mestha et al. |
| 9,697,599 | B2 | 7/2017 | Prasad et al. |
| 9,750,461 | B1 | 9/2017 | Telfort |
| 9,839,756 | B2 | 12/2017 | Klasek |
| 9,943,371 | B2 | 4/2018 | Bresch et al. |
| 2004/0258285 | A1 | 12/2004 | Hansen et al. |
| 2005/0203348 | A1* | 9/2005 | Shihadeh ............ A61B 5/02438 600/300 |
| 2007/0116328 | A1 | 5/2007 | Sablak et al. |
| 2009/0304280 | A1 | 12/2009 | Aharoni et al. |
| 2010/0249630 | A1 | 9/2010 | Droitcour et al. |
| 2011/0144517 | A1 | 6/2011 | Cervantes |
| 2013/0271591 | A1 | 10/2013 | Van Leest et al. |
| 2013/0324876 | A1 | 12/2013 | Bernal et al. |
| 2014/0023235 | A1 | 1/2014 | Cennini et al. |
| 2014/0052006 | A1* | 2/2014 | Lee ...................... A61B 5/7278 600/479 |
| 2014/0275832 | A1 | 9/2014 | Muehlsteff et al. |
| 2014/0378810 | A1 | 12/2014 | Davis et al. |
| 2015/0003723 | A1 | 1/2015 | Huang et al. |
| 2015/0317814 | A1 | 11/2015 | Johnston et al. |
| 2016/0000335 | A1 | 1/2016 | Khachaturian et al. |
| 2016/0049094 | A1 | 2/2016 | Gupta et al. |
| 2016/0082222 | A1* | 3/2016 | Garcia Molina .... A61B 5/0482 600/27 |
| 2016/0174887 | A1 | 6/2016 | Kirenko et al. |
| 2016/0310084 | A1 | 10/2016 | Banerjee et al. |
| 2016/0317041 | A1* | 11/2016 | Porges ................ A61B 5/7235 |
| 2017/0007795 | A1 | 1/2017 | Pedro et al. |
| 2017/0147772 | A1 | 5/2017 | Meehan et al. |
| 2018/0042500 | A1* | 2/2018 | Liao ................... A61B 5/02411 |
| 2018/0104426 | A1 | 4/2018 | Oldfield et al. |
| 2018/0106897 | A1 | 4/2018 | Shouldice et al. |
| 2018/0169361 | A1 | 6/2018 | Dennis et al. |
| 2018/0228381 | A1* | 8/2018 | LeBoeuf ............... A61B 5/222 |
| 2018/0310844 | A1* | 11/2018 | Tezuka .................... G06T 7/11 |
| 2018/0325420 | A1* | 11/2018 | Gigi .................... A61B 5/0816 |

FOREIGN PATENT DOCUMENTS

| | | | | |
|---|---|---|---|---|
| EP | 003207862 | * | 8/2017 | ............ A61B 5/743 |
| EP | 3207863 | | 8/2017 | |
| EP | 3384827 | * | 10/2018 | ............... A61B 5/11 |
| WO | WO2015059700 | | 4/2015 | |
| WO | 2015078735 | | 6/2015 | |
| WO | WO2017060463 | | 4/2017 | |
| WO | WO2017089139 | | 6/2017 | |
| WO | 2018042376 A1 | | 3/2018 | |

OTHER PUBLICATIONS

Wang, W. et al., "Exploiting spatial redundancy of image sensor for motion robust rPPG." IEEE Transactions on Biomedical Engineering, vol. 62, No. 2, pp. 415-425, 2015.
Bruser, C. et al., "Adaptive Beat-to-Beat Heart Rate Estimation in Ballistocardiograms," IEEE Transactions Information Technology in Biomedicine, vol. 15, No. 5, Sep. 2011, pp. 778-786.
Rubinstein, M., "Analysis and Visualization of Temporal Variations in Video", Department of Electrical Engineering and Computer Science, Massachusetts Institute of Technology, Feb. 2014, 118 pages.
Wadhwa, N. et al., "Phase-Based Video Motion Processing," MIT Computer Science and Artificial Intelligence Lab, Jul. 2013, 9 pages.
Wadhwa, N. et al., "Riesz pyramids for fast phase-based video magnification." in Proc. of IEEE International Conference on Computational Photography (ICCP), Santa Clara, CA, pp. 1-10, 2014.
Klaessens J. H. G. M. et al., "Non-invasive skin oxygenation imaging using a multi-spectral camera system: Effectiveness of various concentration algorithms applied on human skin," Proc. of SPIE vol. 7174 717408-1, 2009, 14 pages.
Addison, P. S. et al., "Video-based Heart Rate Monitoring across a Range of Skin Pigmentations during an Acute Hypoxic Challenge," J Clin Monit Comput, Nov. 9, 2017, 10 pages.
Liu, C. et al., "Motion magnification" ACM Transactions on Graphics (TOG), vol. 24, No. 3, pp. 519-526, 2005.
Abbas A. K. et al., "Neonatal non-contact respiratory monitoring based on real-time infrared thermography," Biomed. Eng. Online, vol. 10, No. 93, 2011, 17 pages.
Teichmann, D. et al., "Non-contact monitoring techniques—Principles and applications," in Proc. of IEEE International Conference of the Engineering in Medicine and Biology Society (EMBC), San Diego, CA, 2012, 4 pages.
Li et al., "A Non-Contact Vision-Based System for Respiratory Rate Estimation", 978-1-4244-7929-0/14, 2014, 4 pages.
Kortelainen, J. et al., "Sleep staging based on signals acquired through bed sensor," IEEE Transactions on Information Technology in Biomedicine, vol. 14, No. 3, pp. 776-785, 2010.
Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-522.
Mestha, L.K. et al., "Towards Continuous Monitoring of Pulse Rate in Neonatal Intensive Care Unit with a Webcam," in Proc. of 36th Annual Int. Conf. of the IEEE Engineering in Medicine and Biology Society, Chicago, Il pp. 1-5, 2014.
Fei J. et al., "Thermistor at a distance: unobtrusive measurement of breathing," IEEE Transactions on Biomedical Engineering, vol. 57, No. 4, pp. 988-998, 2010.
Han, J. et al., "Visible and infrared image registration in man-made environments employing hybrid visual features," Pattern Recognition Letters, vol. 34, No. 1, pp. 42-51, 2013.
Wu, H.Y. et al., "Eulerian video magnification for revealing subtle changes in the world," ACM Transactions on Graphics (TOG), vol. 31, No. 4, pp. 651-658, 2012.
Bhattacharya, S. et al., "Unsupervised learning using Gaussian Mixture Copula models," 21st International Conference on Computational Statistics (COMPSTAT 2014), Geneva, Switzerland, 2014, 8 pages.
Huddar, V. et al., "Predicting Postoperative Acute Respiratory Failure in Critical Care using Nursing Notes and Physiological

(56) References Cited

OTHER PUBLICATIONS

Signals," 36th Annual International Conference of IEEE Engineering in Medicine and Biology Society (IEEE EMBC 2014), Chicago, USA, 2014, 4 pages.
Bhattacharya, S. et al., "A Novel Classification Method for Predicting Acute Hypotensive Episodes in Critical Care," 5th ACM Conference on Bioinformatics, Computational Biology and Health Informatics (ACM-BCB 2014), Newport Beach, USA, 2014, 10 pages.
Zhou, J. et al., "Maximum parsimony analysis of gene copy number changes in tumor phylogenetics," 15th International Workshop on Algorithms in Bioinformatics WABI 2015, Atlanta, USA, 13 pages.
Shrivastava, H. et al., "Classification with Imbalance: A Similarity-based Method for Predicting Respiratory Failure," 2015 IEEE International Conference on Bioinformatics and Biomedicine (IEEE BIBM2015), Washington DC, USA, 8 pages.
Rajan, V. et al., "Clinical Decision Support for Stroke using MultiviewLearning based Models for NIHSS Scores," PAKDD 2016 Workshop: Predictive Analytics in Critical Care (PACC), Auckland, New Zealand, 10 pages.
Rajan, V. et al., "Dependency Clustering of Mixed Data with Gaussian Mixture Copulas," 25th International Joint Conference on Artificial IntelligenceIJCAI 2016, New York, USA, 7 pages.
Sengupta, A. et al., "A Statistical Model for Stroke Outcome Prediction and Treatment Planning," 38th Annual International Conference of the IEEE Engineering in Medicine and Biology (Society IEEE EMBC 2016), Orlando, USA,2016, 4 pages.
Reisner, A. et al., "Utility of the Photoplethysmogram in Circulatory Monitoring". American Society of Anesthesiologist, May 2008, pp. 950-958.
Tamura et al., "Wearable Photoplethysmographic Sensors—Past & Present," Electronics, 2014, pp. 282-302.
Poh et al., "Non-contact, automated cardiac pulse measurements using video imaging and blind source separation," Opt. Express 18,10762-10774 (2010), 14 pages.
Kumar, M. et al., "Distance PPG: Robust non-contact vital signs monitoring using a camera," Biomedical optics express 2015, 24 pages.
Colantonio, S. "A smart mirror to promote a healthy lifestyle," Biosystems Engineering, vol. 138, Oct. 2015, pp. 33-43, Innovations in Medicine and Healthcare.
Scalise, Lorenzo, et al., "Heart rate measurement in neonatal patients using a webcamera.", 978-1-4673-0882-3/12, IEEE, 2012, 4 pages.
Javadi M. et al., Diagnosing Pneumonia in Rural Thailand: "Digital Cameras versus Film Digitizers for Chest Radiograph Teleradiology," International Journal of Infectious Disease, Mar. 2006;10(2), pp. 129-135.
Liu H. et al., "A Novel Method Based on Two Cameras for Accurate Estimation of Arterial Oxygen Saturation," BioMedical Engineering OnLine, 2015, 17 pages.
George et al., "Respiratory Rate Measurement From PPG Signal Using Smart Fusion Technique," International Conference on Engineering Trends and Science & Humanities (ICETSH-2015), 5 pages, 2015.
Addison, Paul S. PhD, "A Review of Signal Processing Used in the Implementation of the Pulse Oximetry Phtoplethysmographic Fluid Responsiveness Parameter", International Anesthesia Research Society, Dec. 2014, vol. 119, No. 6, pp. 1293-1306.
McDuff, Daniel J., et al., "A Survey of Remote Optical Photoplethysmographic Imaging Methods", 978-1-4244-9270-1/15, IEEE, 2015, pp. 6398-6404.
Poh, et al., "Advancements in Noncontact, Multiparameter Physiological Measurements Using a Webcam", IEEE Transactions on Biomedical Engineering, vol. 58, No. 1, Jan. 2011, 5 pages.
Addison, Paul S., et al., "Developing an algorithm for pulse oximetry derived respiratory rate (RRoxi): a healthy volunteer study", J Clin Monit Comput (2012) 26, pp. 45-51.

Bickler, Philip E. et al., "Factors Affecting the Performance of 5 Cerebral Oximeters During Hypoxia in Healthy Volunteers", Society for Technology in Anesthesia, Oct. 2013, vol. 117, No. 4, pp. 813-823.
Verkruysse, Wim, et al., "Calibration of Contactless Pulse Oximetry", Anesthiesia & Analgesia, Jan. 2017, vol. 124, No. 1, pp. 136-145.
Cennini, Giovanni, et al., "Heart rate monitoring via remote phtoplethysmography with motion artifacts reduction", Optics Express, Mar. 1, 2010, vol. 18, No. 5, pp. 4867-4875.
Lv, et al., "Class Energy Image Analysis for Video Sensor-Based Gait Recognition: A Review", Sensors 2015, 15, pp. 932-964.
Villarroel, Mauricio, et al., "Continuous non-contact vital sign monitoring in neonatal intensive care unit", Healthcare Technology Letters, 2014, vol. 1, Iss. 3, pp. 87-91.
Bousefsaf, Frederic, et al., "Continuous wavelet filtering on webcam photoplethysmographic signals to remotely assess the instantaneous heart rate", Biomedical Signal Processing and Control 8, 2013, pp. 568-574.
BSI Standards Publication, "Medical electrical equipment, Part 2-61: Particular requirements for basic safety and essential performance of pulse oximeter equipment", BS EN ISO 80601-2-61:2011, 98 pages.
Jopling, Michael W., et al., "Issues in the Laboratory Evaluation of Pulse Oximeter Performance", Anesth. Analg. 2002; 94, pp. S62-S68.
Kong, Lingqin, et al., "Non-contact detection of oxygen saturation based on visible light imaging device using ambient light", Optics Express, Jul. 29, 2013, vol. 21, No. 15, pp. 17464-17471.
Aarts, Lonneke A.M., et al., "Non-contact heart rate monitoring utilizing camera photoplethysmography in the neonatal intensive care unit—A pilot study", Early Human Development 89, 2013, pp. 943-948.
Sun, Yu, et al., "Noncontact imaging phtoplethysmography to effectively access pulse rate variability", Journal of Biomedical Optics, Jun. 2013, vol. 18(6), 10 pages.
Guazzi, Alessandro R., et al., "Non-contact measurement of oxygen saturation with an RGB camera", Biomedical Optics Express, Sep. 1, 2015, vol. 6, No. 9, pp. 3320-3338.
Shao, Dangdang, et al., "Noncontact Monitoring Breathing Pattern, Exhalation Flow Rate and Pulse Transit Time", IEEE Transactions on Biomedical Engineering, vol. 61, No. 11, Nov. 2014, pp. 2760-2767.
Tarassenko, L., et al., "Non-contact video-based vital sign monitoring using ambient light and auto-regressive models", Institute of Physics and Engineering in Medicine, 2014, pp. 807-831.
Shah, Nitin, et al., "Performance of three new-generation pulse oximeters during motion and low perfusion in volunteers", Journal of Clinical Anesthesia, 2012, 24, pp. 385-391.
Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177.
Addison,Paul S., et al., "Pulse oximetry-derived respiratory rate in general care floor patients", J Clin Monit Comput, 2015, 29, pp. 113-120.
Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622.
European Search Report; European Patent Application No. 17156334. 9; Applicant: Covidien LP; dated Jul. 13, 2017, 10 pgs.
Cooley et al. "An Algorithm for the Machine Calculation of Complex Fourier Series," Aug. 17, 1964, pp. 297-301.
European Search Report; European Patent Application No. 17156337. 2; Applicant: Covidien LP; dated Jul. 13, 2017, 10 pgs.
Lai, C. J. et al. "Heated humidified high-flow nasal oxygen prevents intraoperative body temperature decrease in non-intubated thoracoscopy." Journal of Anesthesia. Oct. 15, 2018. 8 pages.
Pereira, C. et al. "Noncontact Monitoring of Respiratory Rate in Newborn Infants Using Thermal Imaging." IEEE Transactions on Biomedical Engineering. Aug. 23, 2018. 10 pages.

(56) References Cited

OTHER PUBLICATIONS

Yu et al. "Motion-compensated noncontact imaging photoplethysmography to monitor cardiorespiratory status during exercise," Journal of Biomedical Optics, vol. 16, No. 7, Jan. 1, 2011, 10 pages.
Ni et al. "RGBD-Camera Based Get-Up Event Detection for Hospital Fall Prevention." Acoustics, Speech and Signal Processing (ICASSP). 2012 IEEE International Conf., Mar. 2012: pp. 1405-1408.
Amelard, et al., "Non-contact transmittance photoplethysmographic imaging (PPGI) for long-distance cardiovascular monitoring," ResearchGate, Mar. 23, 2015, pp. 1-13, XP055542534 [Retrieved online Jan. 15, 2019].
Nisar, et al. "Contactless heart rate monitor for multiple persons in a video", IEEE International Conference on Consumer Electronics—Taiwan (ICCE-TW), May 27, 2016, pp. 1-2, XP032931229 [Retrieved on Jul. 25, 2016].
International Search Report and Written Opinion for International Application No. PCT/US2018/060648, dated Jan. 28, 2019, 17 pages.
International Search Report and Written Opinion for International Application No. PCT/US2018/065492, dated Mar. 8, 2019, 12 pages.

\* cited by examiner

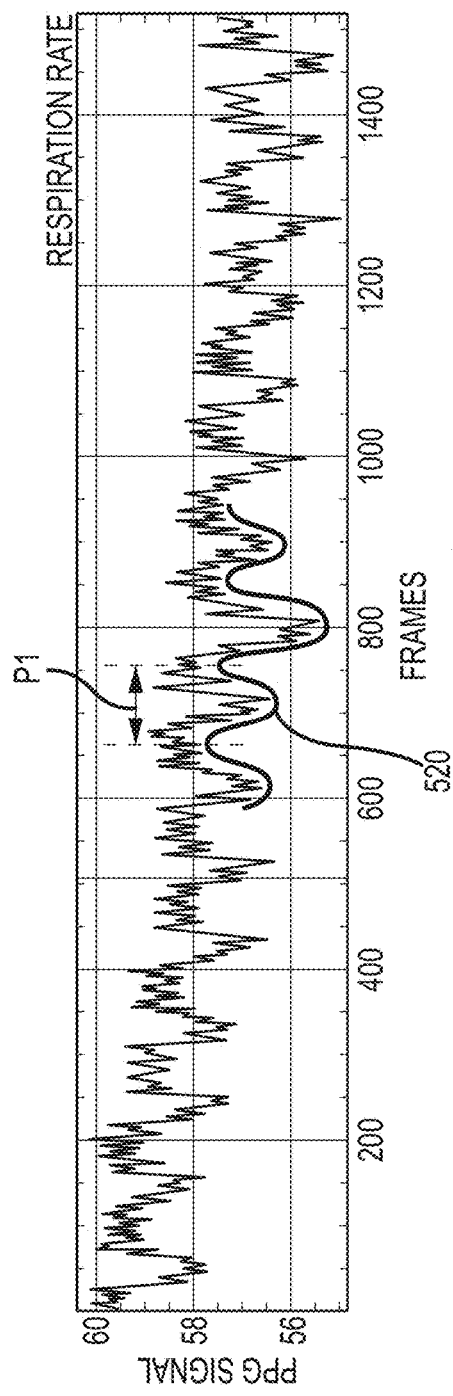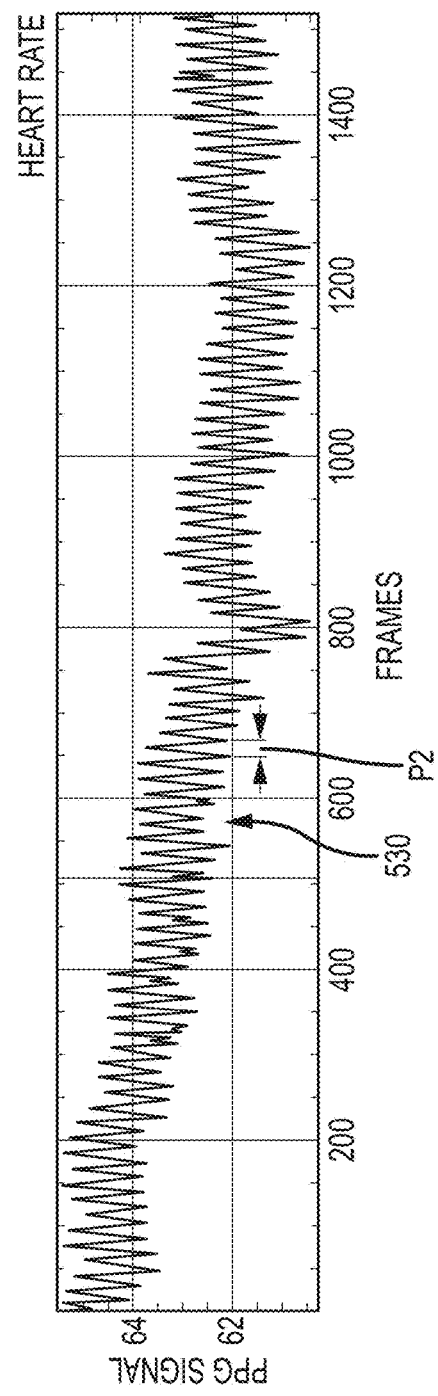

SYSTEMS AND METHODS FOR VIDEO-BASED MONITORING OF VITAL SIGNS

RELATED APPLICATIONS

This application claims priority to and the benefit of U.S. Provisional Application No. 62/297,682 (filed Feb. 19, 2016); U.S. Provisional Application No. 62/335,862 (filed May 13, 2016); and U.S. Provisional Application No. 62/399,741 (filed Sep. 26, 2016), the contents of which are incorporated herein by reference in their entirety.

BACKGROUND

Many conventional medical monitors require attachment of a sensor to a patient in order to detect physiologic signals from the patient and transmit detected signals through a cable to the monitor. These monitors process the received signals and determine vital signs such as the patient's pulse rate, respiration rate, and arterial oxygen saturation. An example of a prior art monitoring system 100 is shown in FIG. 1. The system 100 includes a monitor 110 and a sensor 112 connected to the monitor 110 by a cable 114. In the example of FIG. 1, the monitor 110 is a pulse oximeter, and the sensor 112 is a finger sensor including two light emitters and a photodetector. The sensor 112 emits light into the patient's finger, detects light transmitted through the patient's finger, and transmits the detected light signal through the cable 114 to the monitor 110. The monitor 110 includes a processor that processes the signal, determines vital signs (including pulse rate, respiration rate, and arterial oxygen saturation), and displays them on an integrated display 116.

Other monitoring systems include other types of monitors and sensors, such as electroencephalogram (EEG) sensors, blood pressure cuffs, temperature probes, and others.

Many of these conventional monitors require some type of cable or wire, such as cable 114 in FIG. 1, physically connecting the patient to the monitor. As a result, the patient is effectively tethered to the monitor, which can limit the patient's movement around a hospital room, restrict even simple activities such as writing or eating, and prevent easy transfer of the patient to different locations in the hospital without either disconnecting and connecting new monitors, or moving the monitor with the patient.

Some wireless, wearable sensors have been developed, such as wireless EEG patches and wireless pulse oximetry sensors. Although these sensors improve patient mobility, they introduce new problems such as battery consumption, infection risk from re-use on sequential patients, high cost, and bulky designs that detract from patient compliance and comfort.

Video-based monitoring is a new field of patient monitoring that uses a remote video camera to detect physical attributes of the patient. This type of monitoring may also be called "non-contact" monitoring in reference to the remote video sensor, which does not contact the patient. The remainder of this disclosure offers solutions and improvements in this new field.

BRIEF DESCRIPTION OF THE DRAWINGS

FIG. 5C is a chart of a light intensity signal from a first region of interest according to an embodiment of the invention.

FIG. 5D is a chart of a light intensity signal from a second region of interest according to an embodiment of the invention.

FIG. 10B-1 is a continuation page for FIG. 10B.

SUMMARY

Figure 1:
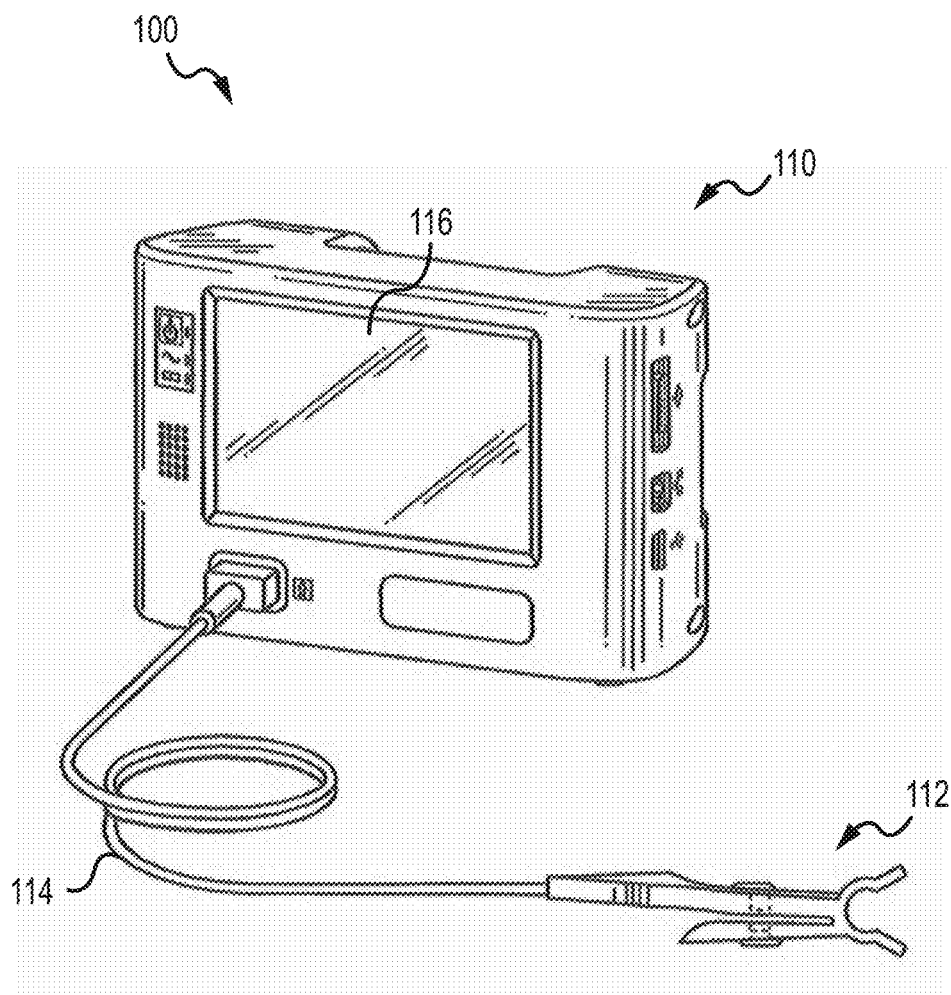
FIG. 1 is a perspective view of a pulse oximetry monitor and sensor according to the prior art.

A calibration strip may be used as explained in more detail below. In an embodiment, a video-based method of measuring a patient's vital sign includes providing a calibration strip comprising a substrate with first and second opposite surfaces, an adhesive on the first surface of the substrate for adhering to a patient, and a visible scale on the second surface for viewing by a video camera; detecting, by the video camera, a first light signal from the scale and a second light signal from the patient, within the same field of view; adjusting a calibration of the video camera based on a measurement of the first light signal; applying the calibration to the second light signal; measuring a vital sign of the patient from the calibrated second light signal; and outputting the measured vital sign for further processing or display.

In an embodiment, the scale comprises a greyscale, and the measurement of the first light signal comprises a measurement of a first intensity of at least a portion of the greyscale. In an embodiment, the method includes, at a later time, measuring a second intensity that differs from the first intensity by an amount, and further adjusting the calibration based on the measured second intensity. In an embodiment, the method also includes further adjusting the calibration based on the second intensity comprises adjusting a coefficient in proportion to the amount. In an embodiment, the method includes determining that the amount exceeds a threshold, prior to adjusting the coefficient. In an embodiment, detecting the second light signal comprises combining light from two or more non-contiguous regions of exposed skin of the patient.

In an embodiment, the scale comprises a color map comprising a plurality of colors, and the measurement of the first light signal comprises a measurement of a color value of one of the plurality of colors. In an embodiment, adjusting the calibration comprises comparing the color value to a reference color value and identifying a difference. In an embodiment, the reference color value comprises a baseline color value measured from the first light signal at a first time. In an embodiment, adjusting the calibration comprises determining that the difference exceeds a threshold, and adjusting a coefficient based on the difference.

In an embodiment, the scale comprises a greyscale, and wherein the measurement of the first light signal comprises a measurement of a white value of the greyscale. In an embodiment, applying the calibration comprises white balancing the first and second light signals.

In an embodiment, the method includes operating a second video camera to monitor a second patient, and adjusting a calibration of the second video camera to match the adjusted calibration of the first video camera.

In an embodiment, the method includes detecting motion based on movement of the scale within the field of view, and generating a motion signal based on the detected motion.

In an embodiment, the method includes measuring oxygen saturation from the calibrated second light signal. The calibrated second light signal comprises two of a red signal, a green signal, and a blue signal, and measuring the oxygen saturation comprises measuring a ratio of the two of the red, green, and blue signals. In an embodiment, detecting the second light signal comprises combining light from two or more non-contiguous regions of exposed skin of the patient.

In an embodiment, the video comprises an optical splitter, and the calibrated second light signal comprises two light signals output from the optical splitter.

In an embodiment, a system for video-based measurement of a patient's pulse rate includes a video camera positioned remote from a patient, the video camera having a field of view encompassing exposed skin of the patient; a calibration strip positioned within the field of view, the calibration strip comprising a scale viewable by the camera; and a hardware memory coupled to the video camera by wired or wireless communication, the memory storing instructions for instructing a processor to: detect a first light intensity signal from the scale and a second light intensity signal from the exposed skin of the patient; adjust a calibration of the video camera based on a measurement of the first light intensity signal; apply the calibration to the second light intensity signal; measure a pulse rate of the patient from the calibrated second light intensity signal; and output the measured pulse rate for further processing or display. In an embodiment, the calibration strip comprises first and second light emitters. In an embodiment, the calibration strip is devoid of a photodetector.

Independent component analysis may be used, as explained in more detail below. In an embodiment, a method for measuring blood oxygen saturation of a patient includes receiving, from a video camera, a video signal encompassing exposed skin of a patient; extracting from the video signal time-varying red, green, and blue signals; decomposing the red, green, and blue signals into a component signal having a primary frequency at a pulse rate of the patient; identifying, in the component signal, an individual pulse representative of a heart beat; locating a corresponding portion of two of the red, green, and blue signals; and measuring blood oxygen saturation of the patient from the located corresponding portions of the two signals.

In an embodiment, the method includes determining and displaying a pulse rate measured from the primary frequency of the component signal. In an embodiment, an audio beep is triggered in synchrony with the located corresponding portion of one of the two signals or in synchrony with the identified individual pulse in the component signal. In an embodiment, the located portions of the two signals comprise cardiac pulses, and, for each of the two signals, the located cardiac pulse is added to a weighted average pulse. In an embodiment, measuring blood oxygen saturation comprises calculating a ratio of ratios of the weighted average pulses of the two signals. In an embodiment, extracting the red, green, and blue signals comprises selecting pixels within the image frame that exhibit a modulation at the primary frequency. In an embodiment, the selected pixels are non-contiguous.

In an embodiment, extracting the red, green, and blue signals comprises selecting pixels within the image frame exhibiting a modulation that is at the primary frequency and that has an amplitude above a threshold.

In an embodiment, a method for measuring a pulse rate of a patient includes receiving, from a video camera, a video signal having a field of view encompassing exposed skin of a patient; identifying, within the video signal, regions of pixels that exhibit a modulation above an amplitude threshold; extracting from the identified regions time-varying red, green, and blue signals; decomposing the red, green, and blue signals into a component signal having a primary frequency at a pulse rate of the patient; measuring the pulse rate from the primary frequency of the component signal; and outputting the measured pulse rate for further processing or display.

In an embodiment, the method also includes identifying, in the component signal, individual pulses representative of individual heart beats; for each identified pulse, locating a corresponding portion of two of the red, green, and blue signals; and measuring blood oxygen saturation of the patient from the located corresponding portions of the two signals.

A frequency accumulator may be used, as explained in more detail below. In an embodiment, a method for video-based monitoring of a patient's pulse rate includes generating a video signal from a video camera having a field of view exposed to a patient, the video signal comprising a time-varying intensity signal for each of a plurality of pixels in the field of view; combining the intensity signals within a region of the field of view to produce a regional intensity signal; transforming the regional intensity signal into the frequency domain to produce a regional frequency signal; over a sliding time window, identifying peaks in the regional frequency signal; over a period of time, accumulating the identified peaks; selecting a median frequency from the accumulated peaks; updating a running average pulse rate of a patient, wherein updating comprises: converting the median frequency into a measured pulse rate; and adding the measured pulse rate to the running average to produce an updated average pulse rate; and outputting the updated average pulse rate for display.

In an embodiment, the period of time is one second. In an embodiment, identified peaks from the accumulated peaks are removed based on an age of the identified peaks. In an embodiment, the method includes, at repeated intervals, discarding the accumulated peaks and repeating the steps of identifying peaks, accumulating peaks, selecting the median frequency, updating the running average pulse rate, and outputting the updated average pulse rate.

In an embodiment, adding the measured pulse rate to the running average comprises applying a weight to the measured pulse rate based on a quality of the regional frequency signal. In an embodiment, the quality of the regional frequency signal is measured by a variability of the accumulated peaks over the period of time. In an embodiment, the quality of the regional frequency signal is measured by an amplitude of the accumulated peaks. In an embodiment, the quality of the regional frequency signal is measured by a signal to noise ratio of the regional frequency signal.

In an embodiment, frequency peaks outside of a physiologic limit are discarded. In an embodiment, the measured pulse rate is discarded when it differs from the average pulse rate by more than a defined amount.

In an embodiment, the method includes updating an average respiration rate of the patient, wherein updating the average respiration rate comprises: selecting a second median frequency from the identified peaks; converting the second median frequency into a measured respiration rate; and adding the measured respiration rate to the average respiration rate to produce an updated average respiration rate; and outputting the updated average respiration rate for display.

In an embodiment, selecting the region of the field of view is based on a strength of modulations of the pixels in the region. In an embodiment, the region comprises two or more non-adjacent groups of pixels.

The frame rate may be adjusted to reject noise, as explained in more detail below. In an embodiment, a method for video-based monitoring of a vital sign of a patient includes receiving a video signal from a video camera having a field of view exposed to a patient, the video signal comprising a time-varying intensity signal for each of a plurality of pixels in the field of view; combining the intensity signals of selected pixels to produce a time-varying regional intensity signal; transforming the regional intensity signal into the frequency domain to produce a regional frequency signal; operating the video camera at a first frame rate during a first period of time, and at a second, different frame rate during a second, subsequent period of time; identifying, in the regional frequency signal, a noise peak at a first frequency during the first period of time that moves to a second, different frequency upon a transition from the first period of time to the second period of time; filtering the regional intensity signal to remove the frequency of the noise peak; and measuring a vital sign of the patient from the filtered regional intensity signal.

In an embodiment, the method also includes identifying a stationary peak that remains stationary in the frequency domain upon the transition from the first period of time to the second period of time, and measuring the vital sign from the identified stationary peak. In an embodiment, the vital sign comprises pulse rate, and measuring the vital sign comprises converting the frequency of the identified stationary peak into the pulse rate. In an embodiment, combining the intensity signals of selected pixels comprises selecting the pixels that exhibit modulations at a shared frequency. In an embodiment, the selected pixels are non-contiguous.

In an embodiment, a method for video-based monitoring of a vital sign of a patient includes receiving a video signal from a video camera having a field of view exposed to a patient, the video signal comprising a time-varying intensity signal for each of a plurality of pixels in the field of view; combining the intensity signals of selected pixels to produce a time-varying regional intensity signal; transforming the regional intensity signal into the frequency domain to produce a regional frequency signal; operating the video camera at a first frame rate during a first period of time, and at a second, different frame rate during a second, subsequent period of time; identifying, in the regional frequency signal, a stationary peak that is stationary upon a transition from the first period of time to the second period of time; and measuring a vital sign of the patient from the identified stationary peak.

In an embodiment, the method also includes identifying, in the regional frequency signal, a noise peak that is non-stationary upon the transition from the first period of time to the second period of time, and filtering the regional intensity signal to remove the noise peak.

In an embodiment, a method for video-based monitoring of a vital sign of a patient includes receiving a video signal from a video camera having a field of view exposed to a patient, the video signal comprising a time-varying intensity signal for each of a plurality of pixels in the field of view; operating the video camera at a frame rate that changes according to a change trajectory over a period of time; combining the intensity signals of selected pixels to produce a combined intensity signal; transforming the combined intensity signal into the frequency domain to produce a frequency signal; identifying, in the frequency signal, a noise peak that moves in synchrony with the change trajectory; filtering the combined intensity signal to remove the noise peak; and measuring a vital sign of the patient from the filtered intensity signal.

In an embodiment, the method also includes identifying, in the frequency signal, a physiologic peak that is stationary over the period of time, and measuring the vital sign from the physiologic peak. In an embodiment, the physiologic peak corresponds to a physiologic frequency of the patient. In an embodiment, the physiologic frequency is pulse rate. In an embodiment, the physiologic frequency has a period that is smaller than the period of time.

In an embodiment, the change trajectory comprises sweeping the frame rate at a constant sweep rate over the period of time. In an embodiment, identifying the noise peak comprises identifying a peak that moves at the sweep rate. In an embodiment, the change trajectory comprises three or more different, discrete frame rates. In an embodiment, the frame rate is fixed after the noise peak has been identified.

In an embodiment, a method for video-based monitoring of a vital sign of a patient includes receiving a video signal from a video camera having a field of view exposed to a patient, the video signal comprising a time-varying intensity signal for each of a plurality of pixels in the field of view; combining the intensity signals of selected pixels to produce a combined intensity signal; transforming the combined intensity signal into the frequency domain over first and second different time windows to produce first and second frequency transforms; identifying, in the first and second frequency transforms, a noise peak that remains stationary in the first and second frequency transforms; filtering the combined intensity signal to remove the noise peak; and measuring a vital sign of the patient from the filtered intensity signal.

A region of interest may be displayed to a user, as explained in more detail below. In an embodiment, a video-based method for measuring a vital sign of a patient includes receiving a video signal from a video camera having a field of view exposed to a patient; displaying on a display screen a portion of the video signal; receiving a first user input from a user, the first user input identifying a location of a first region of interest within the video signal; extracting from the first region of interest a first intensity signal comprising a time-varying intensity of one or more pixels in the first region; measuring a first vital sign of the patient from the first intensity signal; displaying on the display screen a time-varying modulation of the first intensity signal; receiving a second user input from a user, the second user input indicating that the location has been moved to a second, different region of interest; extracting from the second region of interest a second intensity signal comprising a time-varying intensity of one or more pixels in the second region; measuring a second vital sign of the patient from the second intensity signal; and displaying on the display screen a time-varying modulation of the second color signal.

In an embodiment, the first vital sign comprises heart rate and the second vital sign comprises respiration rate. In an embodiment, the modulations of the first and second color signals are displayed on the display screen simultaneously. In an embodiment, the second user input further comprises a path from the first region of interest to the second region of interest, and wherein the method further comprises identifying a plurality of intermediate regions of interest along the path, extracting an intermediate intensity signal from one of the intermediate regions, and displaying on the display screen a modulation of the intermediate intensity signal. In an embodiment, the first region of interest comprises two or more non-adjacent groups of pixels.

In an embodiment, a video-based method for monitoring a patient includes displaying on a display screen a video signal from a video camera having a field of view exposed to a patient; receiving a first user input from a user, the first user input identifying a location of a region of interest within the video signal; extracting from the region of interest a first intensity signal comprising a time-varying intensity of one or more pixels in the region of interest; displaying on the display screen the first intensity signal; receiving from the user a second user input that moves the region of interest along a path; continually updating the location of the region of interest along the path; continually updating the intensity signal extracted from the moving region of interest; and displaying on the display screen the continually updated intensity signal.

In an embodiment, the method also includes identifying a modulation of the intensity signal, and measuring a physiologic rate of the patient from the modulation. In an embodiment, the physiologic rate is pulse rate. In an embodiment, a transform of the intensity signal into the frequency domain is displayed.

DETAILED DESCRIPTION

The present invention relates to the field of medical monitoring, and in particular non-contact, video-based monitoring of pulse rate, respiration rate, motion, activity, and oxygen saturation. Systems and methods are described for receiving a video signal in view of a patient, identifying a physiologically relevant area within the video image (such as a patient's forehead or chest), extracting a light intensity signal from the relevant area, filtering those signals to focus on a physiologic component, and measuring a vital sign from the filtered signals. The video signal is detected by a camera that views but does not contact the patient. With appropriate selection and filtering of the video signal detected by the camera, the physiologic contribution to the detected signal can be isolated and measured, producing a useful vital sign measurement without placing a detector in physical contact with the patient. This approach has the potential to improve patient mobility and comfort, along with many other potential advantages discussed below.

As used herein, the term "non-contact" refers to monitors whose measuring device (such as a detector) is not in physical contact with the patient. Examples include cameras, accelerometers mounted on a patient bed without contacting the patient, radar systems viewing the patient, and others. "Video-based" monitoring is a sub-set of non-contact monitoring, employing one or more cameras as the measuring device. In an embodiment, the camera produces an image stack, which is a time-based sequence of images of the camera's field of view. The camera may be considered a "video" camera if the frame rate is fast enough to create a moving, temporal image signal.

Remote sensing of a patient in a video-based monitoring system presents several new challenges. One challenge is presented by motion. The problem can be illustrated with the example of pulse oximetry. Conventional pulse oximetry sensors include two light emitters and a photodetector. The sensor is placed in contact with the patient, such as by clipping or adhering the sensor around a finger, toe, or ear of a patient. The sensor's emitters emit light of two particular wavelengths into the patient's tissue, and the photodetector detects the light after it is reflected or transmitted through the tissue. The detected light signal, called a photoplethysmogram (PPG), modulates with the patient's heartbeat, as each arterial pulse passes through the monitored tissue and affects the amount of light absorbed or scattered. Movement of the patient can interfere with this contact-based oximetry, introducing noise into the PPG signal due to compression of the monitored tissue, disrupted coupling of the sensor to the finger, pooling or movement of blood, exposure to ambient light, and other factors. Modern pulse oximeters employ filtering algorithms to remove noise introduced by motion and to continue to monitor the pulsatile arterial signal.

However, movement in non-contact pulse oximetry creates different complications, due to the extent of movement possible between the patient and the camera, which acts as the detector. Because the camera is remote from the patient, the patient may move toward or away from the camera, creating a moving frame of reference, or may rotate with respect to the camera, effectively morphing the region that is being monitored. Thus, the monitored tissue can change morphology within the image frame over time. This freedom of motion of the monitored tissue with respect to the detector introduces new types of motion noise into the video-based signals.

Another challenge is the contribution of ambient light. In this context, "ambient light" means surrounding light not emitted by components of the medical monitor. In contact-based pulse oximetry, the desired light signal is the reflected and/or transmitted light from the light emitters on the sensor, and ambient light is entirely noise. The ambient light can be filtered, removed, or avoided in order to focus on the desired signal. In contact-based pulse oximetry, contact-based sensors can be mechanically shielded from ambient light, and direct contact between the sensor and the patient also blocks much of the ambient light from reaching the detector. By contrast, in non-contact pulse oximetry, the desired physiologic signal is generated or carried by the ambient light source; thus, the ambient light cannot be entirely filtered, removed, or avoided as noise. Changes in lighting within the room, including overhead lighting, sunlight, television screens, variations in reflected light, and passing shadows from moving objects all contribute to the light signal that reaches the camera. Even subtle motions outside the field of view of the camera can reflect light onto the patient being monitored. Thus new filtering techniques are needed to isolate the physiologic signal from this combined ambient light signal.

If these challenges are addressed, non-contact monitoring such as video-based monitoring can deliver significant benefits. Some video-based monitoring can reduce cost and waste by reducing usage of disposable contact sensors, replacing them with reusable camera systems. Video monitoring may also reduce the spread of infection, by reducing physical contact between caregivers and patients (otherwise incurred when the caregiver places, adjusts, or removes the contact sensor on the patient). Some remote video cameras may improve patient mobility and comfort, by freeing patients from wired tethers or bulky wearable sensors. This untethering may benefit patients who need exercise and movement. In some cases, these systems can also save time for caregivers, who no longer need to reposition, clean, inspect, or replace contact sensors. Another benefit comes from the lack of sensor-off alarms or disruptions. A traditional contact-based system can lose the physiologic signal when the contact sensor moves or shifts on the patient, triggering alarms that are not actually due to a change in physiology. In an embodiment, a video-based system does not drop readings due to sensors moving or falling off the patient (sensor-off) or becoming disconnected from the monitor (sensor-disconnect), and thus can reduce nuisance alarms. In an embodiment, a video-based monitor, such as a pulse oximeter, operates without sensor-off or sensor-disconnect alarms. For example, a video-based monitor can trigger an alarm based on stored alarm conditions, where the stored alarm conditions omit a sensor-off or sensor-disconnect alarm.

Figure 2A:
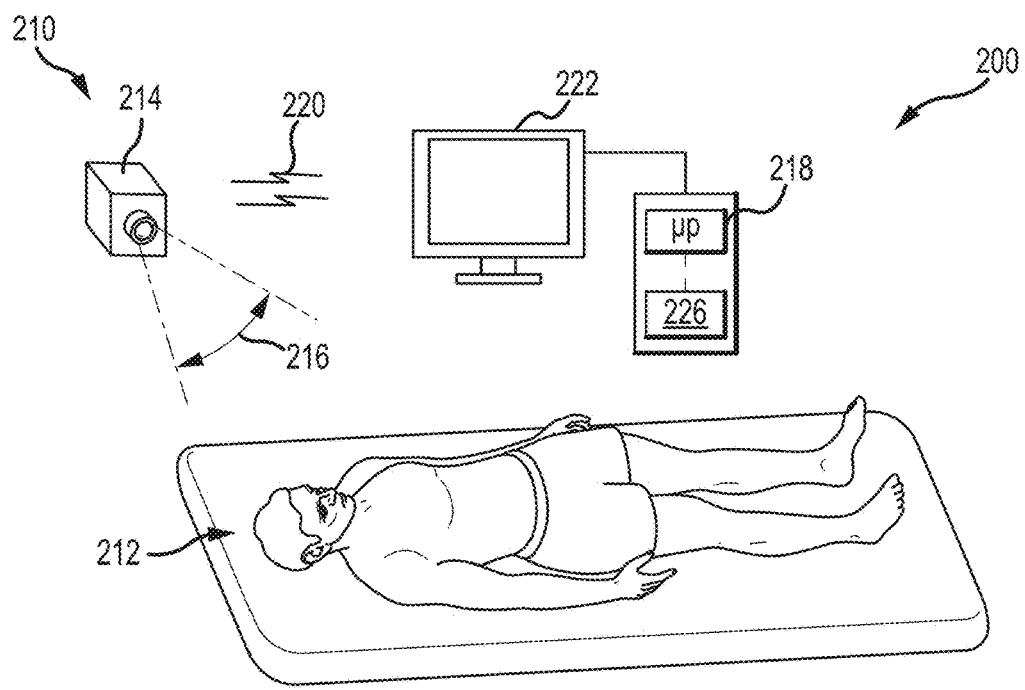
FIG. 2A is schematic view of a video-based patient monitoring system according to an embodiment of the invention.

Various embodiments of the present invention are described below, to address some of these challenges. FIG. 2A shows a video-based remote monitoring system 200 and a patient 212, according to an embodiment. The system 200 includes a non-contact detector 210 placed remote from the patient 212. In this embodiment, the detector 210 includes a camera 214, such as a video camera. The camera 214 is remote from the patient, in that it is spaced apart from and does not contact the patient. The camera includes a detector exposed to a field of view 216 that encompasses at least a portion of the patient 212. In some embodiments, the field of view 216 encompasses exposed skin of the patient, in order to detect physiologic signals visible from the skin such as arterial oxygen saturation (SpO2 or SvidO2). The camera generates a sequence of images over time. A measure of the amount, color, or brightness of light within all or a portion of the image over time is referred to as a light intensity signal. In an embodiment, each image includes a two-dimensional array or grid of pixels, and each pixel includes three color components—for example, red, green, and blue. A measure of one or more color components of one or more pixels over time is referred to as a "pixel signal," which is a type of light intensity signal. The camera operates at a frame rate, which is the number of image frames taken per second (or other time period). Example frame rates include 20, 30, 40, 50, or 60 frames per second, greater than 60 frames per second, or other values between those. Frame rates of 20-30 frames per second produce useful signals, though frame rates above 50 or 60 frames per second are helpful in avoiding aliasing with light flicker (for artificial lights having frequencies around 50 or 60 Hz).

The detected images are sent to a monitor 224, which may be integrated with the camera 214 or separate from it and coupled via wired or wireless communication with the camera (such as wireless communication 220 shown in FIG. 2A). The monitor 224 includes a processor 218, a display 222, and hardware memory 226 for storing software and computer instructions. Sequential image frames of the patient are recorded by the video camera 214 and sent to the processor 218 for analysis. The display 222 may be remote from the monitor 224, such as a video screen positioned separately from the processor and memory.

Figure 2B:
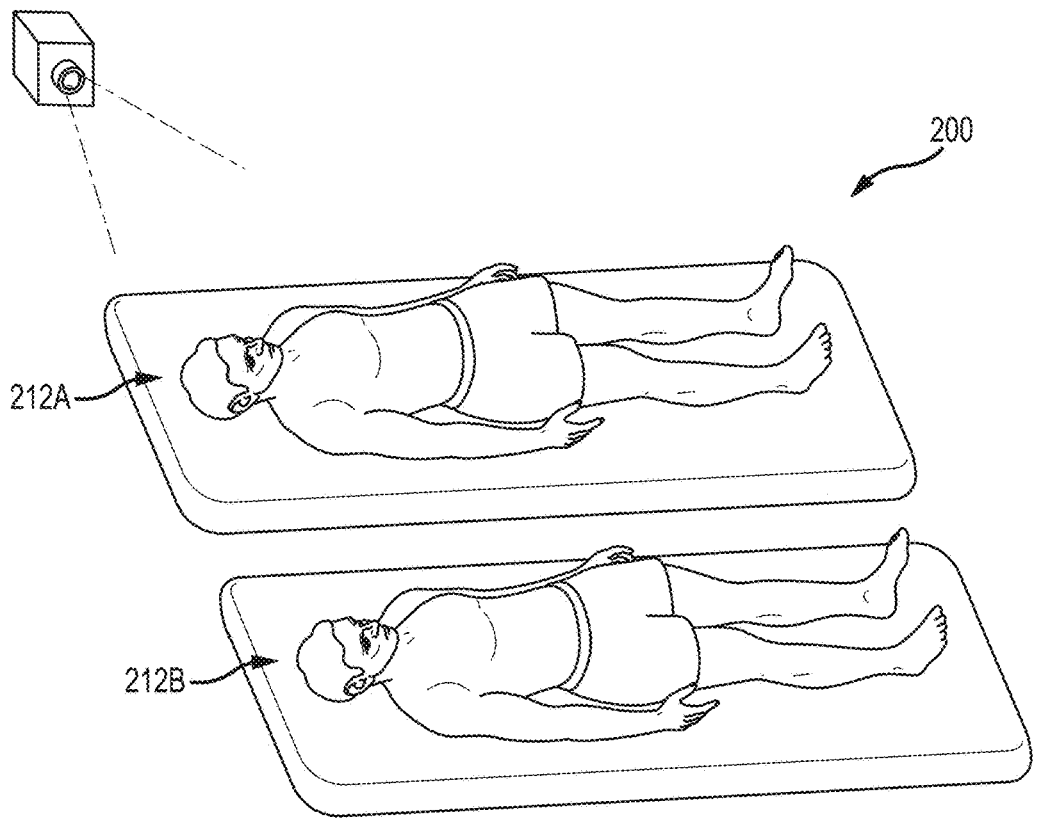
FIG. 2B is schematic view of a video-based patient monitoring system monitoring multiple patients according to an embodiment of the invention.

FIG. 2B shows the system 200 being implemented to monitor multiple patients, such as patients 212A and 212B. Because the detector 214 in the system is non-contact, it can be used to monitor more than one patient at the same time. A method for this implementation will be described in further detail below.

Figure 3A:
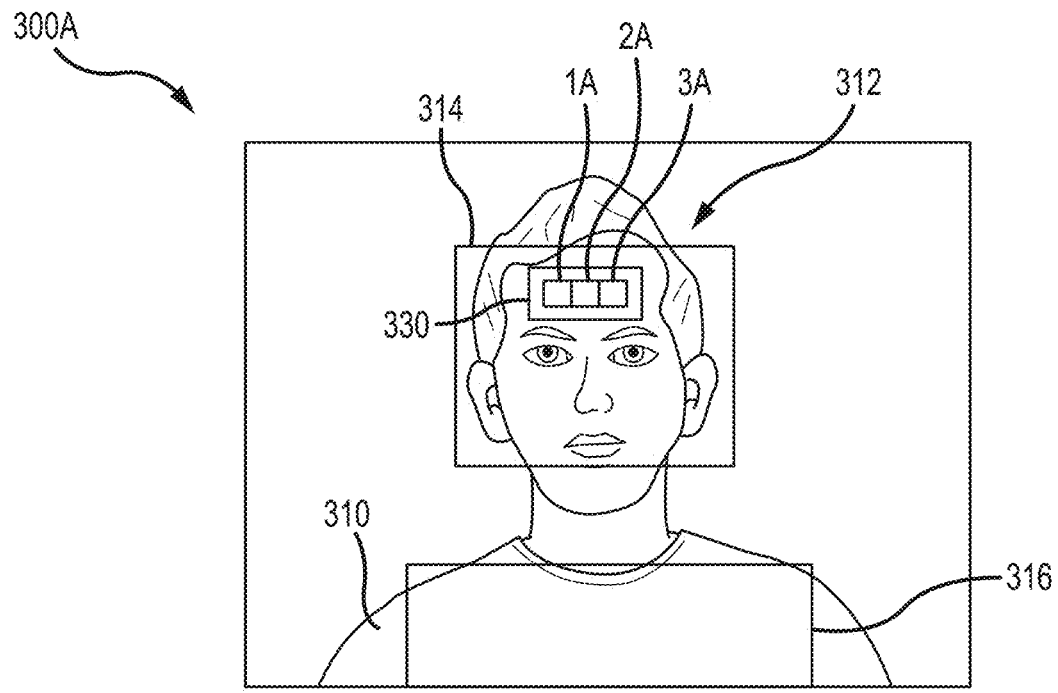
FIG. 3A depicts an image frame from a video signal according to an embodiment of the invention.
Figure 3B:
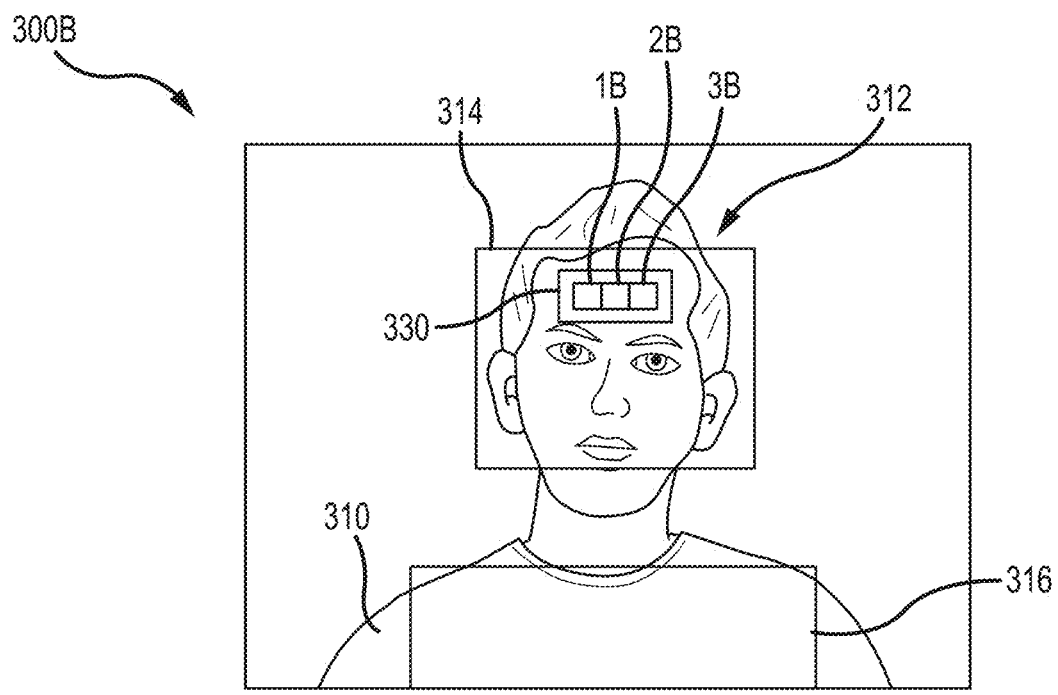
FIG. 3B depicts an image frame from a video signal according to an embodiment of the invention.

Two example image frames 300A and 300B are shown in FIGS. 3A and 3B, respectively. In an embodiment, these image frames are recorded by the system 200. Each image frame includes a patient's head 312 and upper torso 310 in the field of view. The processor has identified a head region 314 within each image frame 300A, 300B. The head region 314 includes at least a portion of the patient's head, such as the face. In some embodiments, the processor also infers a chest region 316, based on the size and location of the head region 314 and empirical ratios of head and chest sizes and shapes. For example, from a rectangular face region of width w and height h, a forehead region may be inferred of a size 0.7*w and 0.3*h, centered horizontally and positioned with its top edge moved down from the top of the face region by a distance 0.25*h. From the same rectangular face region, a chest region may also be inferred at a size of 2*w and 0.75*h, centered horizontally and positioned with its top edge below the bottom of the face region by a distance 0.25*h.

In an embodiment, the video camera records multiple sequential image frames (such as image frames 300A and 300B) that each include the head region 314 and chest region 316. The pixels or detected regions in these sequential images exhibit subtle modulations caused by the patient's physiology, such as heartbeats and breaths. In particular, the color components of the pixels vary between the frames based on the patient's physiology. In one embodiment, the camera employs the Red/Green/Blue color space and records three values for each pixel in the image frame, one value each for the Red component of the pixel, the Blue component, and the Green component. Each pixel is recorded in memory as these three values, which may be integer numbers (typically ranging from 0 to 255 for 8-bit color depth, or from 0 to 4095 for 12-bit color depth) or fractions (such as between 0 and 1). Thus, three one-dimensional vectors for each pixel in the field of view can be extracted from the video signal.

These Red, Green, and Blue values change over time due to the patient's physiology, though the changes may be too subtle to be noticed by the naked human eye viewing the video stream. For example, the patient's heartbeat causes blood to pulse through the tissue under the skin, which causes the color of the skin to change slightly—causing the value corresponding to the Red, Green, or Blue component of each pixel to go up and down. These changes in the pixel signals can be extracted by the processor. The regions within the field of view where these changes are largest can be identified and isolated to focus on the physiologic signal. For example, in many patients, the forehead is well-perfused with arterial blood, so pixels within the patient's forehead exhibit heartbeat-induced modulations that can be measured to determine the patient's heartrate.

To focus on this physiologic signal, the processor identifies a region of interest (ROI) within the image frame. In an embodiment, the region of interest includes exposed skin of the patient, such that the physiologic properties of the skin can be observed and measured. For example, in the embodiment of FIG. 3A, one region of interest includes a forehead region 330, which includes part of the patient's forehead. The processor determines the location of the patient's forehead within the head region 314, for example based on empirical ratios for a human face, and divides the forehead into distinct regions, for example, regions 1A, 2A, and 3A. In another embodiment, the region of interest does not include exposed skin. For example, in FIG. 3A, another region of interest includes the chest region 316 (which may be covered by clothing, bedding, or other materials on the patient). Pixels in this region may fluctuate with the patient's respiration rate, enabling that rate to be measured even without viewing exposed skin of the patient.

Within an individual region of interest, the Red components of the pixels in that region are combined together to produce one time-varying Red pixel signal from that region. The same is done for the Blue and Green pixels. The result is three time-varying pixel signals from each region, and these are plotted in FIG. 4A. The plots in FIG. 4A are derived from the regions 1A, 2A, 3A, and 316 of FIG. 3A. FIG. 4A also shows a plot labeled "Combined Forehead." The Combined Forehead plot shows the combined pixel signals from all three identified regions 1A, 2A, and 3A, meaning that the Red components from all three regions are combined together and plotted over time, as are the Green components and the Blue components. Different sub-sets of regions can be combined together to produce different combinations of pixel signals. Though three forehead regions 1A, 2A, and 3A are shown in FIG. 3A, the forehead, or any other area of interest, can be sub-divided into more or fewer regions, in various shapes or configurations. (Other examples are described in more detail below with reference to FIGS. 5A and 5B.) Pixel signals can be combined by summing or averaging or weighted averaging. In an embodiment, the combined pixel signals are obtained by averaging the Red (or Blue, or Green) color values of the pixels within the region, so that regions of different sizes can be compared against each other.

The pixels within a region may be combined together with a weighted average. For example, within a region, some pixels may exhibit stronger modulations than other pixels, and those stronger-modulating pixels can be weighted more heavily in the combined pixel signal. A weight can be applied to all of the pixels that are combined together, and the weight can be based on quality metrics applied to the modulating intensity signal of each pixel, such as the signal to noise ratio of the intensity signal, a skew metric, an amplitude of a desired modulation (such as modulations at the heart rate or respiration rate), or other measurements of the signal. Further, some pixels within the region may be chosen to be added to the combined pixel signal for that region, and other pixels may be discarded. The chosen pixels need not be adjacent or connected to each other; disparate pixels can be chosen and combined together to create the resulting signal.

The plots in FIG. 4A show a clear pattern of repeating modulations or pulses over time. The pulses in each region 1A, 2A, 3A and in the Combined Forehead plot are caused by the patient's heart beats, which move blood through those regions in the patient's forehead, causing the pixels to change color with each beat. The heart rate of the patient can be measured from these signals by measuring the frequency of the modulations. This measurement can be taken via a frequency transform of the signal (discussed below with reference to FIG. 10A and FIG. 4B) or via a pulse recognition algorithm that identifies each pulse in the signal (for example, by pulse size and shape, by zero crossings, maximums, or minimums in the derivative of the signal, and/or by checking the skew of the derivative of the signal to identify a pulse as a cardiac pulse, which has a characteristically negative skew). The modulations in the plot of the Chest region, in FIG. 4A, are caused by the patient's breaths, which cause the chest to move in correspondence with the breathing rate. The patient's breathing/respiration rate can be measured from this signal in the same way as just described for the heart rate (except for the skew approach). Respiration rate can be identified from a region of the patient that moves with each breath, such as the chest, but need not include exposed skin.

Figure 4B:
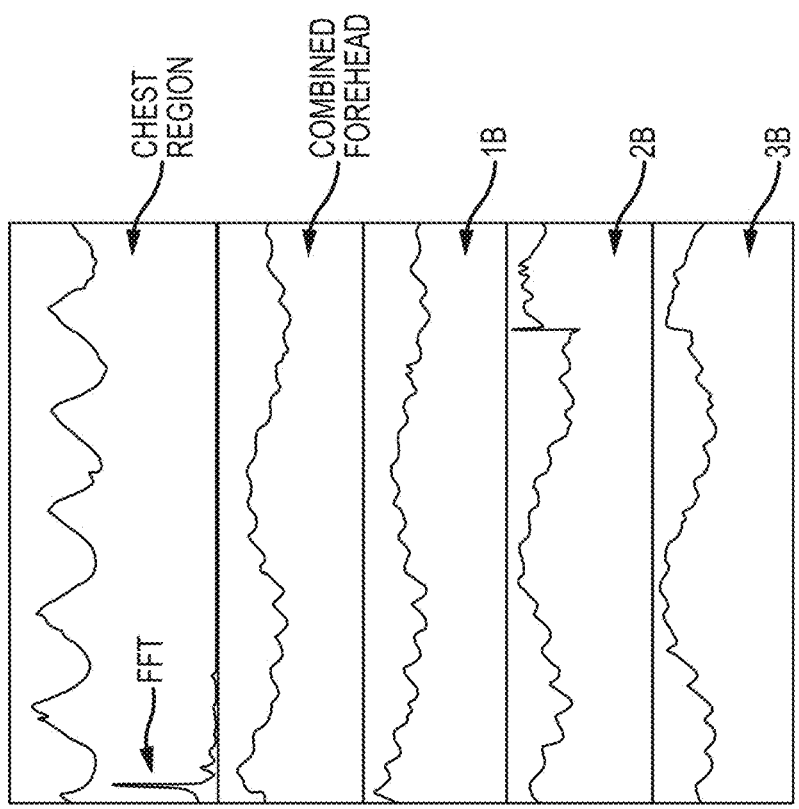
FIG. 4B depicts light intensity signals from the video signal of FIG. 4A.
Figure 4A:
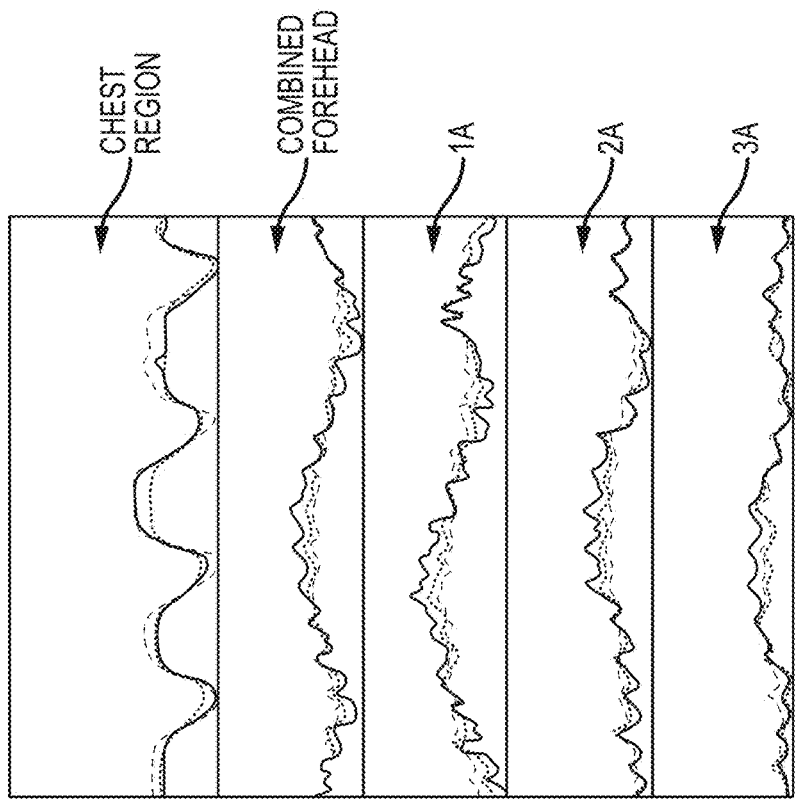
FIG. 4A depicts light intensity signals from the video signal of FIG. 3A.

FIG. 4B shows plots of the pixel streams from the corresponding regions in FIG. 3B. However, in this case, the individual Red, Green, and Blue values within each region have been combined together, such as by summing or averaging, to produce one time-varying signal from each region instead of three separate Red, Green, and Blue signals. By viewing one combined signal from each region, the frequency of the heart rate or respiration rate may emerge more clearly. FIG. 4B also shows a Fast Fourier Transform (FFT) in the Chest Region plot. The FFT identifies the frequency content of the Chest signal, which reveals a primary frequency peak and harmonics. The primary frequency peak is the patient's respiration rate.

Though many embodiments herein are described with reference to pixels and pixel values, this is just one example of a detected light intensity signal. The light intensity signals that are detected, measured, or analyzed may be collected from larger regions or areas, without differentiating down to groups of pixels or individual pixels. Light signals may be collected from regions or areas within an image, whether or not such regions or areas are formed from pixels or mapped to a spatial grid. For example, time-varying light signals may be obtained from any detector, such as a camera or light meter, that detects a unit of light measurement over time. Such units of light measurement may come from individual pixels, from groups or clusters of pixels, regions, sub-regions, or other areas within a field of view. It should also be noted that the term "pixel" includes larger pixels that are themselves formed from aggregates, groups, or clusters of individual pixels.

In an embodiment, the Red, Green, and Blue values from the camera are converted into different color spaces, and the color space that provides the largest or most identifiable physiologic modulations is chosen. In an embodiment, color values are converted into a combination of a color value and a separate brightness value, so that changes in room brightness can be analyzed independently of color or hue. Alternative color spaces (such as YCrCb, CIE Lab, CIE Luv) can separate light intensity from chromatic changes better than the RGB color space. Processing the chromatic component in those spaces can reveal physiological modulation better than in RGB space, when overall scene light intensity is changing. Assessing pixel signals based on chromatic channels in these spaces can increase the robustness of the algorithm and/or increase the range of conditions in which physiological signal extraction is possible. Though the Red/Green/Blue color scheme is often presented here in the examples, it should be understood that other color schemes or color spaces can be utilized by these systems and methods.

Figure 5A:
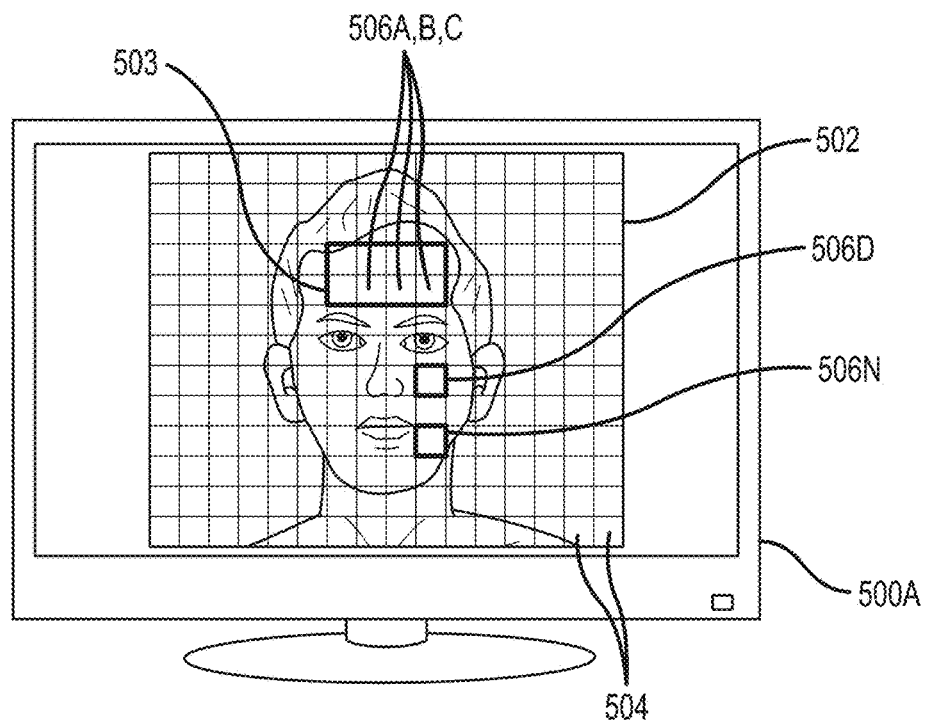
FIG. 5A depicts an image frame according to an embodiment of the invention.
Figure 5B:
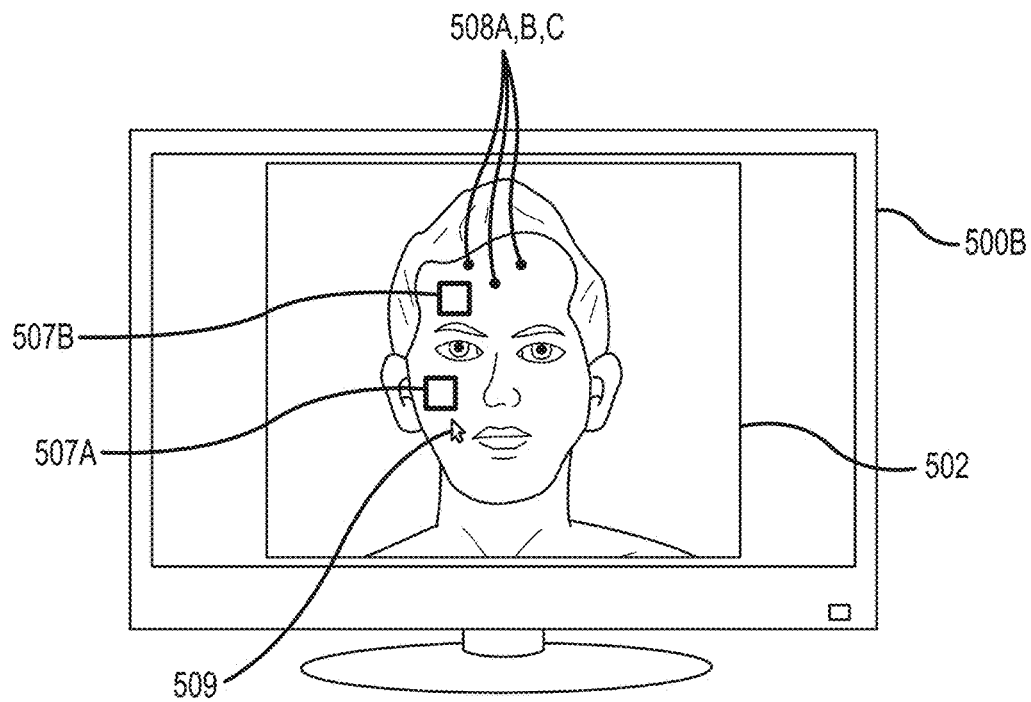
FIG. 5B depicts an image frame according to an embodiment of the invention.

FIGS. 3A and 3B depict five regions of interest—three squares in the forehead, the combination of all three squares together, and one rectangular chest region. In other embodiments, regions of interest can have various shapes, configurations, or combinations. Examples are shown in FIGS. 5A and 5B. In the embodiment of FIG. 5A, a monitor 500A displays an image frame 502, which depicts a region of interest on a patient, in this case a face region, and in particular a forehead region 503. The face region is further divided into a grid 504, segmenting the face region into smaller individual regions. Within this grid 504, individual regions of interest 506A, 506B, 506C, 506D, . . . 506N are identified. The regions of interest 506A-N are regions that include pixels or detected areas that exhibit a physiologic characteristic of the patient. A sub-set of the regions of interest can be chosen to focus on a particular physiologic characteristic that is reflected in the pixels in those regions.

In one embodiment, the selected regions of interest (for measurement of a vital sign) are completely enclosed within the patient region, such as the face or a smaller area such as the forehead. For example, in FIG. 5A, the regions 506A-C are completely contained within the patient's forehead region 503. No portion of regions 506A-C includes pixels outside of the patient's forehead. These regions 506A-C are used to identify a physiologic signal and calculate a vital sign, such as the patient's heartrate, as described above. By enclosing the regions within a physiological area, such as the forehead, according to some embodiments, the signal to noise ratio of the desired physiologic signal increases.

In another embodiment, the selected regions of interest may be non-adjacent to each other, or non-contiguous. For example, in FIG. 5A, non-adjacent regions 506A and 506D may both include pixels that exhibit large modulations correlated with the patient's heartrate, as compared to the other regions. Regions located over large arteries may exhibit larger modulations with heartrate than other regions, for example. In an embodiment, the intensity signals from regions 506A and 506D are averaged together to create a combined signal, and the heartrate measured from that combined signal. Different non-adjacent regions may be chosen for other vital signs, such as respiration rate or oxygen saturation. In an embodiment, heart rate and oxygen saturation are calculated from a combined signal from a first group of non-adjacent pixels or regions, and respiration rate is calculated from a different combined signal from a second, different group of non-adjacent pixels or regions.

In an embodiment, regions of interest within the image frame are selected based on the modulations exhibited by the pixels in each region. Within an image frame, a sub-set of regions may be first identified as candidate regions for further processing. For example, within an image frame, an area of exposed skin of a patient is identified by facial recognition, deduction of a forehead region, user input, and/or skin tone detection. These areas are identified as the regions of interest for further processing. In an embodiment, facial recognition is based on Haar-like features (employing a technique that sums pixel intensities in various regions and differences between sums). A method includes identifying these regions of interest, extracting pixel signals from each region, quantifying the magnitude of physiological modulations exhibited by each pixel signal, selecting regions with strong modulations (such as modulations with an amplitude above a threshold), combining the selected pixel signals together (such as by averaging), and measuring a vital sign from the combined signal. In an embodiment, all sub-regions (such as grids) in the image (or a portion of the image, such as a patient region) are processed, and grid cells that exhibit coherent pulsatile components are combined to generate the pixel signals from which the physiologic measurements are taken.

Selecting non-adjacent regions enables the system to focus on the pixels or regions that carry the physiologic signal with the highest signal to noise ratio, ignoring other areas in the image frame that are contributing a relatively higher degree of noise, such as pixels that do not vary much with heart rate, but that might vary due to a passing shadow or patient movement. The system can focus on pixels that represent the desired vital sign, thereby increasing the signal-to-noise ratio (SNR) of the analyzed signal. With signals from several regions available, the signals with the strongest SNR can be chosen, and signals with weak SNR can be discarded. The chosen signals can be combined together to produce a signal with a strong physiologic component.

Referring to FIG. 5A, the size of the cells within the grid 504 can affect the computation of the resulting pixel signals. If the cells in the grid are very small (such as 10 pixels by 10 pixels), the number of cells increases, causing the number of computations and available signals to increase. The variability of the signals also increases with very small cell sizes. For example, a passing shadow or a twitch can affect a very small area of skin. If a region of interest is wholly contained within that affected area, the signal from that region will become noisy. Larger regions provide a degree of spatial smoothing that reduces susceptibility to such noise, but regions that are too large in size may obscure the physiologic signal. An example of a region of a good size for processing a physiologic signal is approximately one square centimeter (though more or less may also be useful—for example a whole forehead may be used, or an individual pixel). If far away from the subject, a camera may use less pixels. The selection of region size also depends on the resolution of the image, which may depend on the available hardware. Moreover, resolution and frame rate may be inter-related, in that increasing resolution may reduce frame rate. A compromise is necessary between high enough resolution to capture the modulating pixels, and a fast enough frame rate to track those modulations over time. Frame rates over 10 Hz are sufficient for cardiac pulses, and over 2-3 Hz for respiration modulations. Frame rates above about 50 or 60 frames per second are generally less subject to aliasing frequencies introduced by artificial lighting. Sampling from a few hundred pixels (such as over 200 or over 300 pixels) has been sufficient to isolate a physiologic modulation above ambient noise.

The selected regions of interest can change over time due to changing physiology, changing noise conditions, or patient movement. In each of these situations, criteria can be applied for selecting a pixel, group of pixels, or region into the combined signal. Criteria are applied to enhance the physiologic signals by reducing or rejecting contributions from stationary or non-stationary non-physiologic signals. Criteria can include a minimum SNR, a minimum amplitude of physiologic modulations, a minimum variability of the frequency of modulations (to reject non-physiologic, static frequencies), a skew metric (such as modulations that exhibit a negative skew), pixels with values above a threshold (in the applicable Red, Green, or Blue channel), pixels that are not saturated, or combinations of these criteria. These criteria can be continually applied to the visible pixels and regions to select the pixels that meet the criteria. Some hysteresis may be applied so that regions or pixels are not added and removed with too much chatter. For example, pixels or regions must meet the criteria for a minimum amount of time before being added to the combined signal, and must fail the criteria for a minimum amount of time before being dropped. In another example, the criteria for adding a pixel or region to the combined signal may be stricter than the criteria for removing the pixel or region from the combined signal.

For example, in an example involving motion, when the patient turns his or her head, the regions of interest that previously demonstrated heart rate with the best amplitude are no longer visible to the camera, or may be covered in shadow or over-exposed in light. New regions of interest become visible within the field of view of the camera, and these regions are evaluated with the criteria to identify the best candidates for the desired vital sign. For example, referring to FIG. 5A, cells or groups of pixels at the edges of the forehead region 503 can be added or removed from the combined signal during motion as they enter and exit the forehead region. This method enables the monitoring system to continue to track the vital sign through movement of the patient, even as the patient moves or rotates with respect to the camera.

Selected regions may also change over time due to changing physiology. For example, these regions can be updated continually or periodically to remove pixels that do not satisfy the criteria for vital sign measurement, and add new pixels that do satisfy the criteria. For example, as the patient's physiology changes over time, one region of the forehead may become better perfused, and the pixels in that region may exhibit a stronger cardiac modulation. Those pixels can be added to the combined light signal to calculate the heart rate. Another region may become less perfused, or changing light conditions may favor some regions over others. These changes can be taken into account by adding and removing pixels to the combined signal, to continue tracking the vital sign.

Selected regions may also change over time due to changing noise conditions. By applying the criteria over time, pixels or regions that become noisy are removed from the combined light intensity signal, so that the physiologic signal can continue to be monitored via pixels or groups that are less noisy. These updates can be made continually.

In another embodiment, as shown in FIG. 5B, individual pixels 508A-N within the image frame 502, rather than regions or groups of contiguous pixels, are selected and summed together to produce a signal from which a patient vital sign can be measured. In FIG. 5B, the patient region need not be divided into sub-regions, such as the grid 504 shown in FIG. 5A. Rather, individual pixels 508 within the patient region are evaluated, and the pixels that modulate in correlation with the desired vital sign are selected and summed together. These pixels need not be adjacent or in a near vicinity of each other.

Figure 5E:
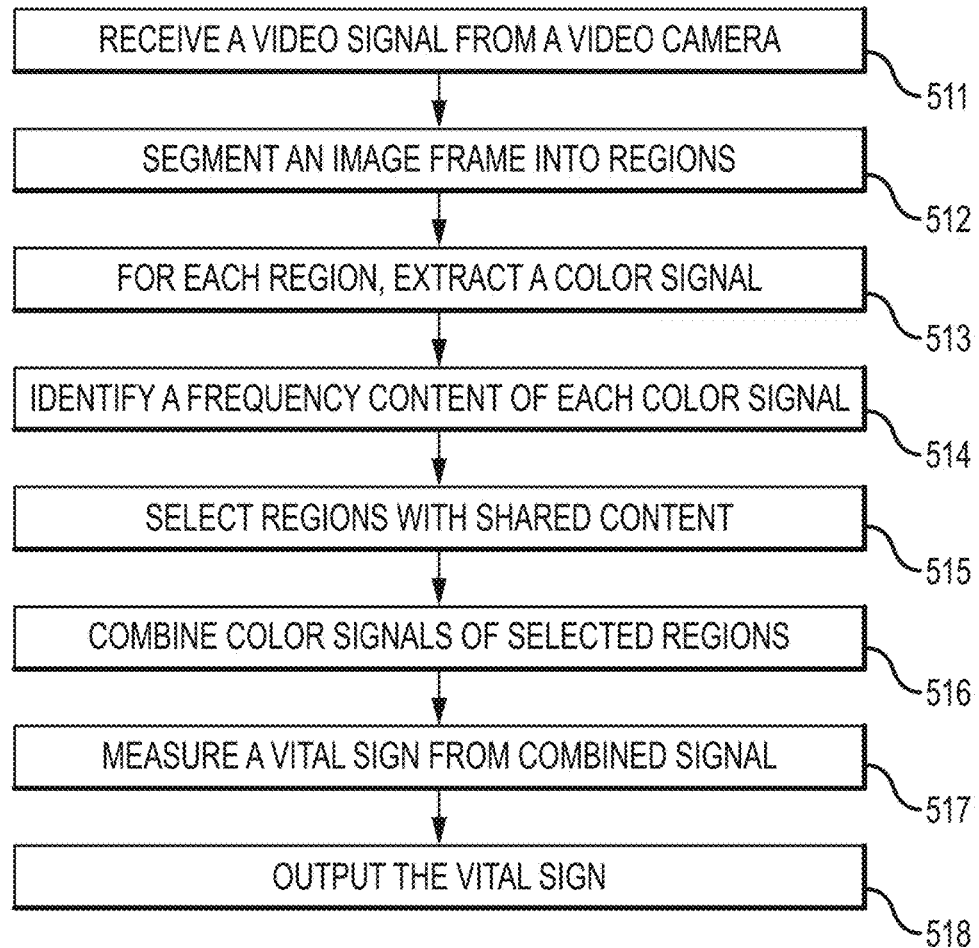
FIG. 5E is a flowchart of a method for measuring a vital sign from a combined region of interest according to an embodiment of the invention.

FIG. 5E shows a method for video-based monitoring of a patient's vital signs, according to an embodiment. The method includes receiving a video signal from a video camera at 511. The video signal includes a plurality of sequential image frames, each image frame having a field of view that includes exposed skin of a patient, such as the face or forehead. The method includes segmenting a first image frame into a plurality of regions at 512, and then, for each region, extracting from the video signal a time-varying color signal at 513. In an example, three time-varying color signals are extracted from each region, corresponding to red, green, and blue pixel values. The method includes identifying a frequency content of each color signal at 514, and selecting regions that have a shared frequency content at 515. The shared frequency content is a modulation at a shared frequency. For example, two regions that both exhibit color signals that modulate at the patient's heart rate, such as a frequency of 60 beats per minute, are selected. In an embodiment, the shared modulation must pass criteria, such as those described above, to select the desired regions. For example, an amplitude threshold for the modulation frequency can be applied as a criterion for selecting regions. In an embodiment, the regions that satisfy this criterion are non-adjacent to each other; they do not need to be in contact with each other or next to each other on the patient. Rather, regions that exhibit a shared modulation at a physiologic frequency, above a noise threshold, are selected even if they are located at disparate, non-contiguous locations across the patient.

Once the desired regions are selected, the method includes combining the color signals of the selected regions at 516, and measuring a vital sign from the combined color signal at 517, such as measuring heart rate from the identified frequency. The vital sign is output for further processing or display at 518. The calculated vital sign can be added to a long-term running average, or a weighted average, where the weight is based on quality metrics such as signal to noise ratio or vital sign variability.

The combined light signal can be used to calculate statistics, such as an amplitude of the physiologic frequency (in the time or frequency domain), a variability of the frequency over time, a variability of the intensity or color of the selected pixels over time, a skew of the modulations, or a signal to noise ratio. Skew is a useful metric because cardiac pulses tend to have a negative skew. Thus, modulations of pixels that exhibit a negative skew may be more likely to be physiologic. In an embodiment, one or more statistics are calculated, and then used to apply a weight to each color signal (from an individual pixel or from a region) that is being combined. This method results in a weighted average that applies more weight to the pixels that exhibit modulations that are stronger or more likely to be physiologic. For example, pixels that modulate with a strongly negative skew, or a high signal to noise ratio, can be weighted more heavily. The criteria used to select regions can also be used to assign weights; for example, regions or pixels that meet a first, stricter set of criteria may be combined with a first, higher weight, and regions or pixels that meet a second, looser set of criteria may be combined with a second, lower weight.

In an embodiment, a weight can also be applied to the vital sign that is calculated from the combined light signal. Each time the vital sign is calculated, a weight can be determined based on current quality measures or statistics from the combined light signal. The newly calculated vital sign is then added to a longer-term running average, based on the weight. For example, the patient's heart rate can be calculated from the combined light signal once per second. An associated weight can be calculated based on the criteria applied to the combined light signal. The weight is reduced when statistics indicate that the light signal may be unreliable (for example, the amplitude of the modulations drops, or the frequency becomes unstable, or the intensity changes suddenly) and increased when statistics indicate that the light signal is reliable.

Furthermore, different combinations of pixels (and/or regions) may be selected for different vital signs of the patient. For example, a first group of pixels and/or regions is summed together to produce a signal that modulates with heart rate, and a second group of pixels and/or regions is summed together to produce a signal that modulates with respiration rate. This approach is demonstrated in FIGS. 5C and 5D, which each show a light intensity signal over the same span of time from the same video signal for the same patient, from different regions, such as groups of pixels. The pixels chosen for the plot in FIG. 5C exhibit relatively large fluctuations correlated with the patient's respiration. This is shown by the large baseline modulations 520, with period P1, in the plotted pixel signal. The frequency of the modulations 520 is the patient's respiration rate, such as 5-20 breaths per minute. By contrast, the pixels chosen for the plot in FIG. 5D do not fluctuate as dramatically with the patient's respiration, but they do fluctuate with the patient's heart rate, as shown by the modulations 530 with shorter period P2. The frequency of these modulations is the patient's heart rate, such as 40-200 beats per minute. These two different plots shown in FIGS. 5C and 5D reflect different vital signs of the patient, based on the same video stream from the same camera taken over a single period of time. By creating combined pixel signals from appropriately selected pixels or regions, various physiologic signals emerge from the video images.

Accordingly, in an embodiment, a method is provided for measuring different vital signs from different regions. These groups can include individual pixels, disparate pixels, contiguous regions, non-contiguous regions, and combinations of these. Pixels combined into one group exhibit a common modulation, such as a frequency of modulation of color or intensity. For example, heart rate can be measured from the frequency of modulation of a first group of pixels, and respiration rate can be measured from the frequency of modulation of a second group of pixels. Oxygen saturation can be measured from either group; in one embodiment, oxygen saturation is measured from the pixels that show strong modulation with heart rate. Specifically, oxygen saturation is measured as a ratio of ratios of the cardiac pulsatile components of two of the signals (such as Red and Green, or Red and Blue) (as described in more detail below).

In an embodiment, a user can view a video image, specify a region of interest, and drag and drop the region across the video image to view changes in modulations in real-time. For example, referring to FIG. 5B, a monitor 500B displays a video image 502 that accepts inputs from a user. A user can use mouse pointer 509 (or other input) to highlight a first area 507A, and view the resulting pixel signals such as the signal shown in FIG. 5C and vital signs measured from that signal. The user can then drag and drop the area of interest to a second area 507B and view the resulting signal and vital signs, such as the signal shown in FIG. 5D. In this way, the user can view in realtime how the modulations of the signal change based on the selected area of interest. In area 507A, the video signal shows strong respiration modulations (see FIG. 5C), while in area 507B, the video signal shows strong cardiac modulations (see FIG. 5D). The user can view the video signal in real-time as it moves along the path from 507A to 507B, to see how the modulations change as the region of interest moves. The user can also view the pixel signals shown in FIGS. 5C and 5D at the same time, to evaluate different vital signs from different regions of interest, at the same time.

Figure 5F:
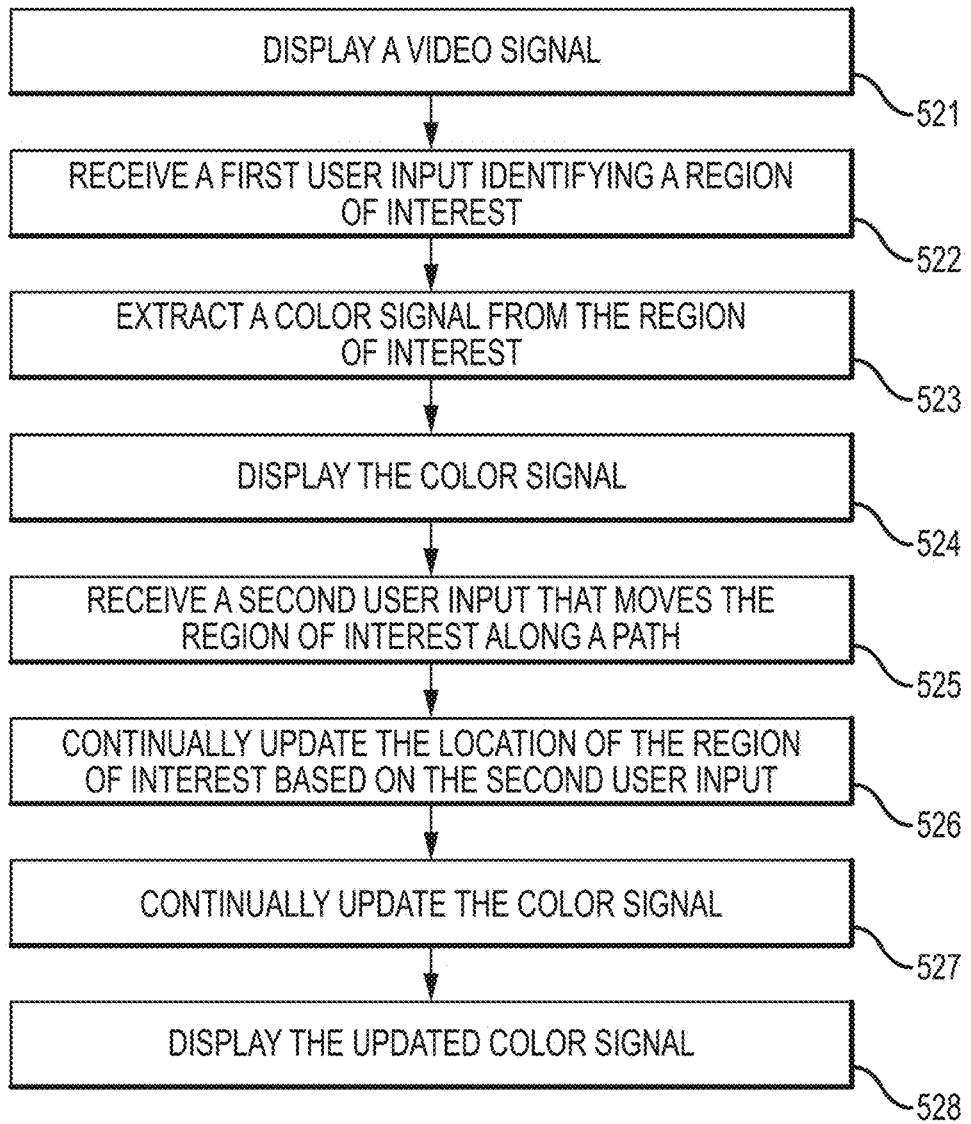
FIG. 5F is a flowchart of a method for dynamically updating and displaying a color signal from a moving region of interest according to an embodiment of the invention.

A method for monitoring a patient by viewing these different modulations across different regions of interest is outlined in FIG. 5F. The method includes displaying a video signal at 521, and receiving a first user input identifying a region of interest within the video image at 522. The method includes extracting a color signal from the region of interest at 523, and displaying the color signal at 524. The method then includes receiving a second user input that moves the region of interest along a path (such as from 507A to 507B in FIG. 5B) at 525. The method includes continually updating the location of the region of interest in accordance with the second user input at 526, continually updating the color signal from the region of interest at 527, and displaying the updated color signal at 528. This enables a user to dynamically change the region of interest and view the resulting extracted video signal, to dynamically see the modulations at any point in the field of view. In addition to displaying the color signal, vital signs can be calculated from the moving region of interest and displayed to the user.

In an embodiment, a video-based method for measuring a vital sign of a patient includes receiving a video signal, displaying on a display screen an image frame from the video signal, and receiving from a user a first user input that identifies a location of a first region of interest within the image frame. The method includes extracting from the first region of interest a first color signal comprising a time-varying intensity of one or more pixels in the first region, detecting a modulation of the first color signal, and measuring a first vital sign of the patient from the modulation of the first color signal. The first vital sign and/or the modulation may be displayed. The method also includes receiving a second user input indicating that the location has been moved to a second, different region of interest. The method then includes extracting from the second region of interest a second color signal, detecting a modulation of the second color signal, measuring a second vital sign of the patient from the modulation of the second color signal, and displaying the modulation and/or second vital sign. In an embodiment, the method includes identifying a plurality of intermediate regions of interest along the path from the first to the second region of interest, extracting an intermediate color signal from one of the intermediate regions, and displaying on the display screen a modulation of the intermediate color signal.

Figure 6A:
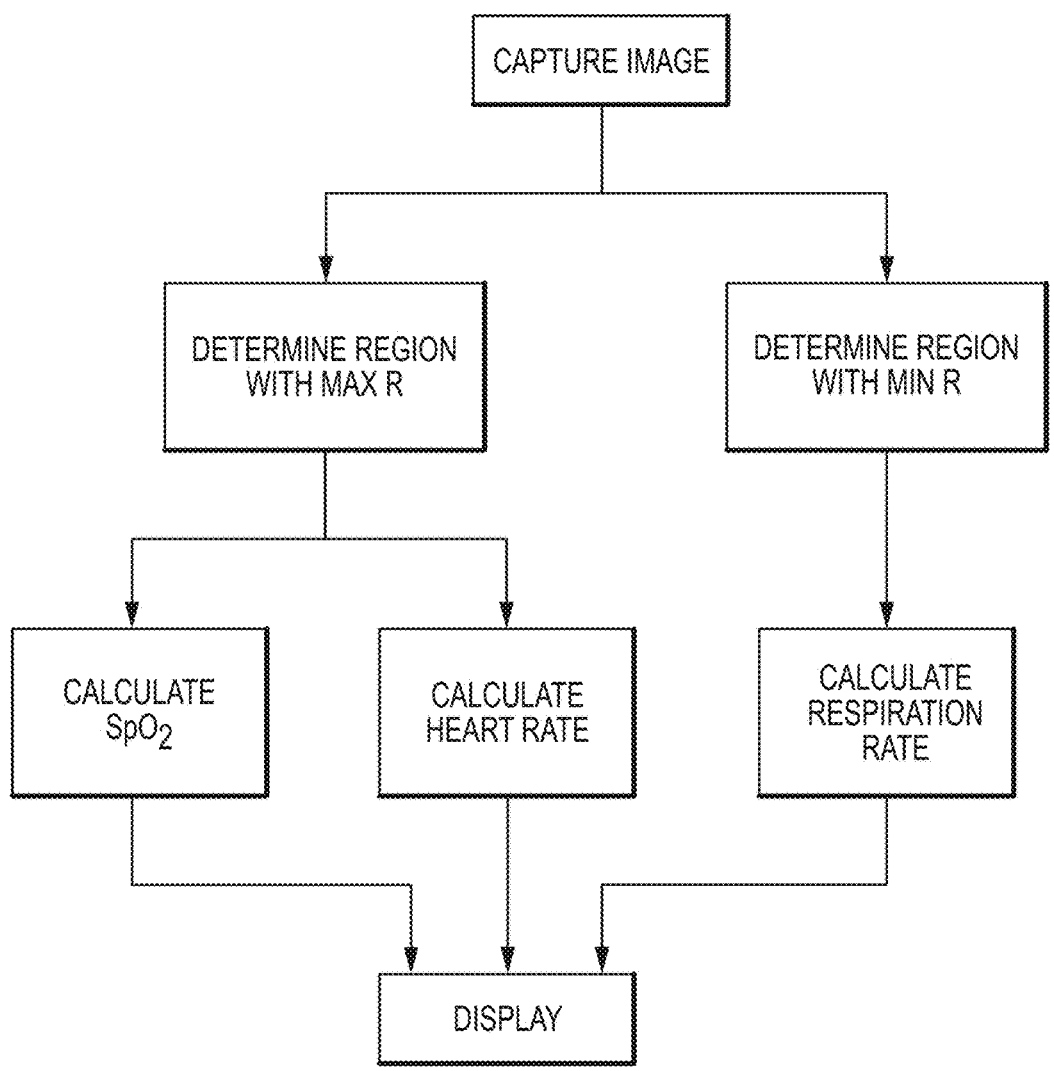
FIG. 6A is a flowchart of a method of determining vital signs from a video signal according to an embodiment of the invention.

In an embodiment, the desired pixels are chosen based on a ratio of modulations in the pixel signals. A ratio R is defined as $A_H/A_R$, where $A_H$ is the cardiac pulse amplitude, and $A_R$ is the respiratory modulation amplitude. The region where R is maximum (or above a suitable threshold) can be used to determine heart rate, and the region where R is minimum (or below a suitable threshold) can be used to determine respiratory rate. A method according to this embodiment is shown in FIG. 6A. Regions may be increased or decreased in size, or discrete regions or pixels combined together, to obtain a combined pixel signal with an optimal or desired ratio R.

As discussed above, a region of interest can be formed based on pixels that modulate with the patient's heart rate. Heart rate can then be calculated from the frequency content of that pixel signal. An example method for calculating heart rate is shown in FIG. 10B. The method includes capturing video, acquiring and averaging color signals (shown as pR, pG, and pB for "photoplethysmogram" red, green, and blue) within a well-perfused ROI, de-noising the signal, performing an FFT (fast Fourier transform) operation over a sliding time window (such as 20 seconds) to identify frequency components of the signals, finding peak frequencies, and accumulating peaks over a period of time (such as one second). De-noising includes filtering the signal to remove noise sources and frequencies outside of a known physiologic range. Examples of filtering operations to remove noise are described below with reference to FIGS. 17A and 17B. In accumulating peaks, the method may add frequencies multiple times based on their relative height, and may add harmonics of already-added frequencies only once. Frequency peaks are added to the accumulator at the frame rate, such as 25-30 times per second.

Then, once per second, the method finds a median frequency from the accumulated ones, and determines heart rate from the median frequency. The determined heart rate is added to an ongoing average, and then posted for display. As noted in the figure, different averaging techniques may be employed for the externally-posted heart rate as well as for an internally-maintained running average, such as to apply additional smoothing to the externally-posted heart rate. When multiple peaks are present, additional filtering can be applied to determine the most likely heart rate. For example, frequency peaks outside of known physiologic limits for heart rate (such as below 40 or above 250 beats per minute) are rejected. Knowledge of the patient's previous heart rate is also useful, as the heart rate is unlikely to jump a large amount (such as 2.5% of the current heart rate, or another percentage, or a value such as 15 or 20 beats per minute) within 1 second, so such frequency peaks can be rejected as noise. Within the acceptable peaks, the strongest peak is selected as the patient's heart rate. When the median frequency is rejected as noise, the previously-calculated heart rate is held for one additional second, while the next group of peaks is accumulated, and the range for an acceptable heart rate is increased. When the new group of peaks is assessed, a median frequency picked, and a new heart rate calculated, the acceptable range is re-set to its normal size, around the new average heart rate. The same method can be used to determine respiration rate, within different frequency ranges and time windows, applied to the same or different pixel signals.

FIG. 10B also includes a cross-correlation process that cross-correlates the frequency spectrums of the three color signals to amplify the results. All four resulting spectrums are analyzed to select and accumulate peaks. A cross correlated spectrum can be calculated by multiplying or summing existing spectrum together. An individual spectrum can be scaled before being combined based on signal quality. For example, because most RGB cameras have twice the number of green pixels compare to red and blue ones, the Green signal is usually better and can be weighted above Red and Blue. This method can follow the strongest peaks around the spectrum over time, as the patient's physiology (such as respiration rate and heart rate) changes.

In an embodiment, a method for monitoring a patient's heart rate includes generating a video signal from a video camera having a field of view encompassing exposed skin of a patient. The video signal includes a time-varying intensity signal for each of a plurality of pixels in the field of view. The method includes combining the intensity signals within a region of the field of view to produce a regional intensity signal, and transforming the regional intensity signal into the frequency domain to produce a regional frequency signal. The region may be selected based on a strength of modulations of intensity signals in the region. The region may include non-adjacent areas or pixels. Over a sliding time window, peaks in the regional frequency signal are identified, and then over a period of time (such as one second), the identified peaks are accumulated. The method includes selecting a median frequency from the identified peaks, and updating a running average heart rate of a patient, which includes converting the median frequency into a measured heart rate and adding the measured heart rate to the running average. The updated average heart rate is output for display. The method may also include removing identified peaks from the accumulated peaks when they reach an age limit. The method may also include discarding frequency peaks outside of a physiologic limit, or discarding the measured heart rate when it differs from the average heart rate by more than a defined amount. The method may also include discarding frequency peaks if they are sub-harmonics of already identified peaks.

Figure 10A:
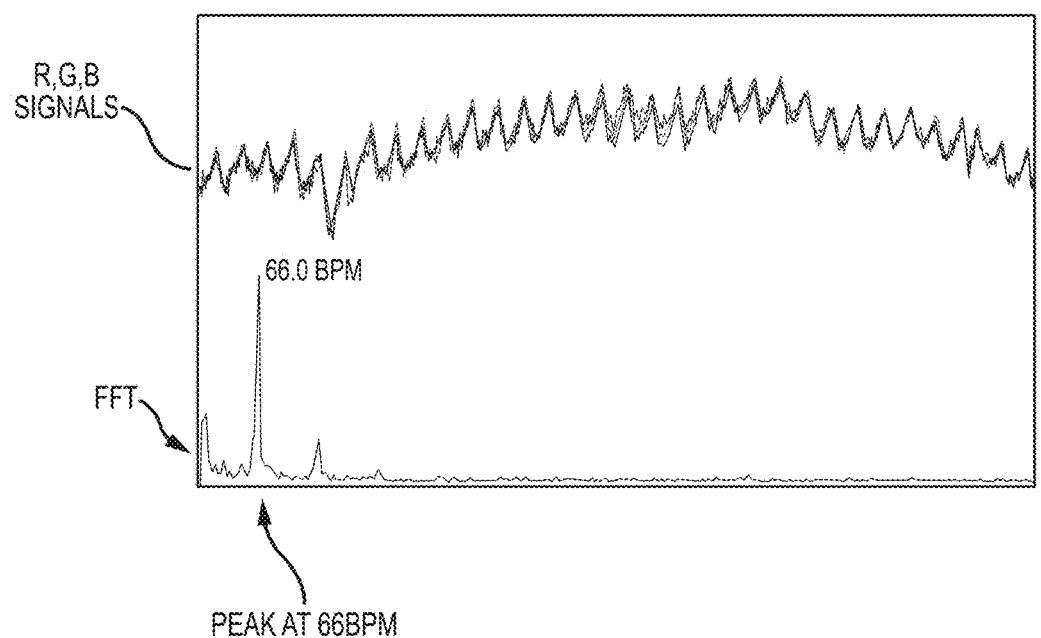
FIG. 10A is a chart of red, green, and blue pixel signals over time and a corresponding frequency transform according to an embodiment of the invention.
Figure 10B:
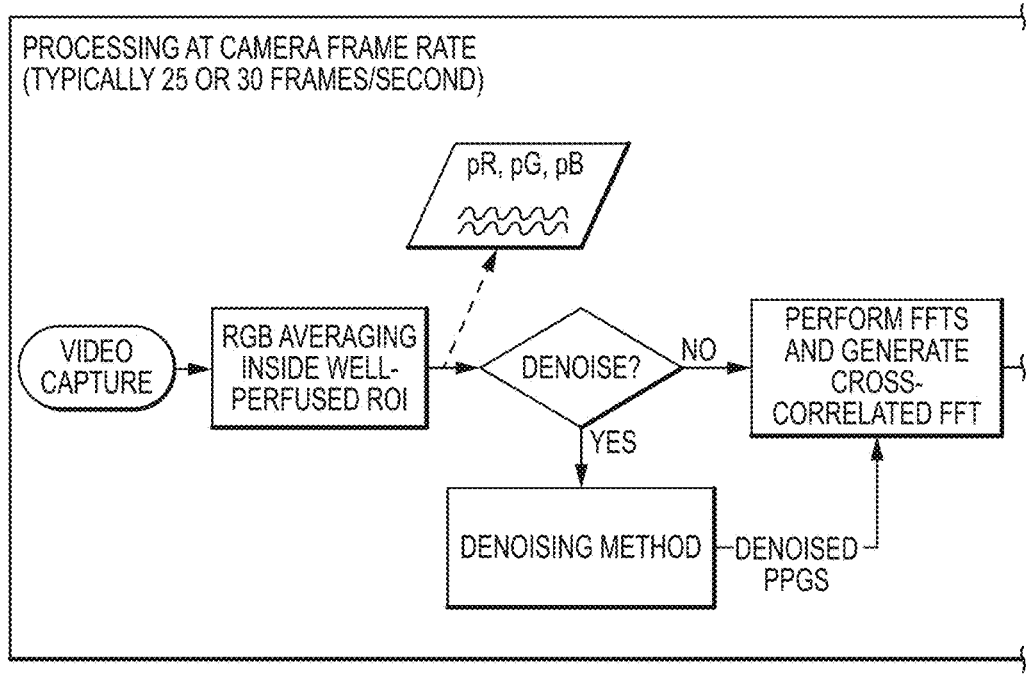
FIG. 10B is a flowchart of a method of calculating heart rate from a video signal utilizing a frequency accumulator, according to an embodiment of the invention.
Figure 10B:
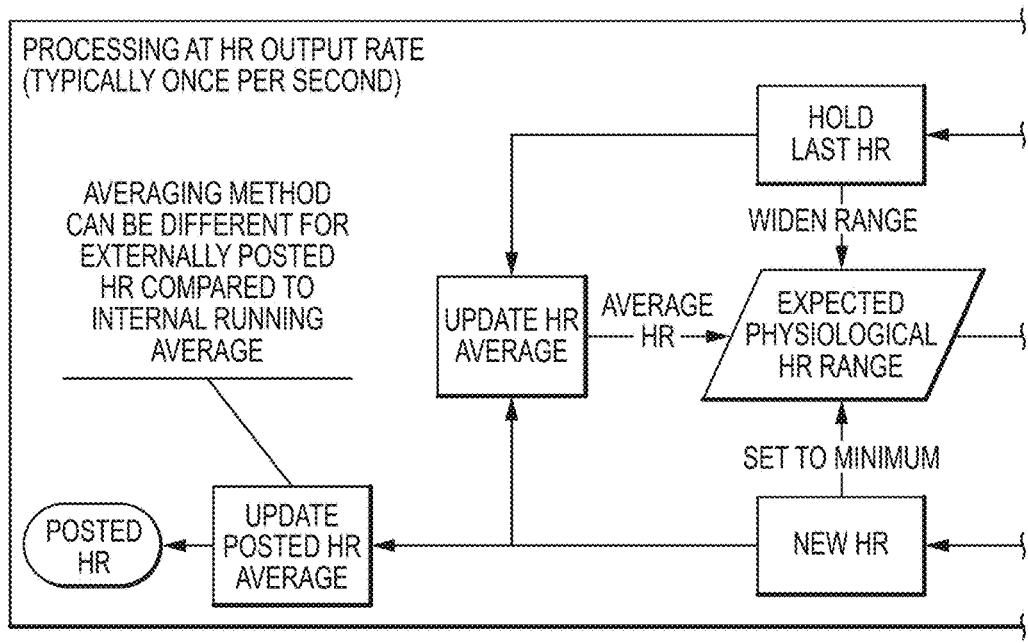
Figures 1, 10B:
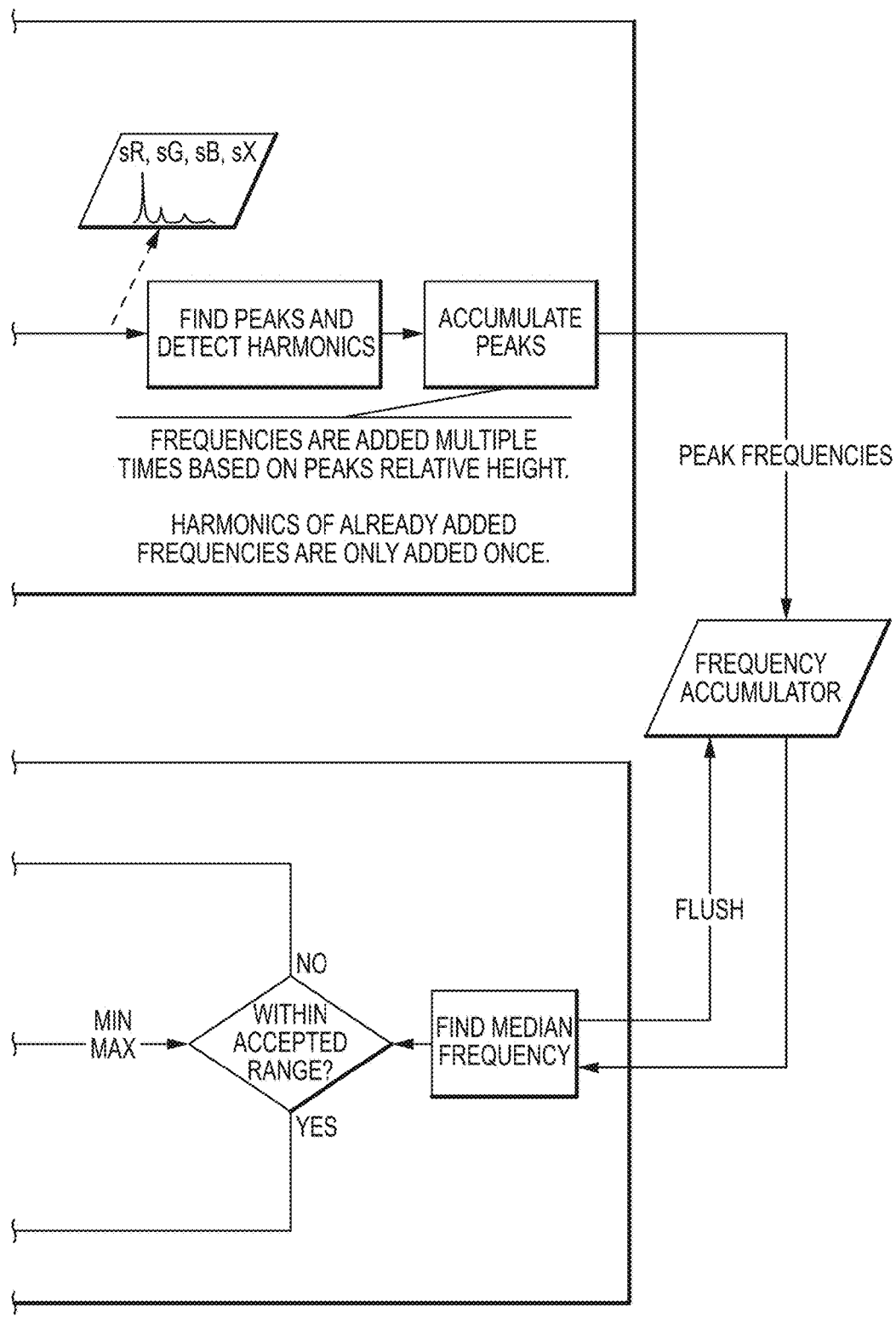

An example frequency transform of a pixel signal from a region of interest is shown in FIG. 10A. This figure shows three (Red, Green, and Blue) pixel signals over time and the FFT operation, which is applied to a 20-second window of the cross-correlated spectrum of all three signals. The FFT shows a strong peak at 66.0 beats per minute. In the method of FIG. 10B, these peaks are added to the frequency accumulator, the median peak is identified, and the patient's heart rate calculated from the median peak.

The non-contact video monitoring system provides many benefits over traditional contact sensors, and also enables monitoring in new and difficult situations. In one example, the non-contact video-based monitoring system can be used to measure vital signs in patients who are not able to tolerate a contact-based sensor, such as patients with skin trauma. These patients could include burn victims, or patients with other sensitive skin conditions. In another example, the non-contact video-based monitoring system can be used to measure multiple patients at the same time (see FIG. 2B). A method for monitoring two or more patients at the same time includes orienting the field of view of the camera to encompass two or more patients. In an embodiment, the camera is oriented such that the field of view encompasses exposed skin of each patient, and groups of pixels that exhibit physiologic modulations are identified for each respective patient. A single camera system can then be used to measure vital signs from multiple patients, such as patients on a general care floor, or to track movement of patients within a room or ward.

The vital signs measured from the video signal can be used to trigger alarms based on physiologic limits (for example, high or low heart rate, SpO2, or respiration rate alarms). The video signals, the measured vital signs, and triggered alarms can be used by clinicians to identify patients in distress, provide clinical intervention, apply a treatment, support a diagnosis, or recommend further monitoring. The vital signs measured from the video signals may be further processed to arrive at a final value that can be displayed or compared to alarm limits. Further processing may include adding the vital sign to a running average (such as an infinite impulse response filter) to smooth out variability, rejecting outlier vital sign measurements that are not supported by known physiological limits (such as a newly calculated heart rate that varies by more than a physiologically expected amount, as discussed above), increasing or decreasing a weight applied to the vital sign, calculating statistics relating to the vital sign, or other processing steps. The result is a final number, derived from the vital sign measurement from the intensity signal, and this final derived number can be displayed, stored, or compared to alarm limits.

Oxygen Saturation

According to an embodiment of the invention, the Red/Green/Blue pixel streams from identified areas of the patient's exposed skin can be used to determine arterial oxygen saturation (SpO2). Traditional pulse oximeters employ contact-based sensors, which include two emitters (typically light emitting diodes, LED's) and a photodetector. The emitters are positioned on the sensor to emit light directly into the patient's skin. The emitters are driven sequentially, so that light of each wavelength can be separately detected at the photodetector, resulting in two time-varying light intensity signals. The wavelengths are chosen based on their relative absorption by oxygenated hemoglobin in the blood. Typically one wavelength falls in the red spectrum and the other in infrared. The patient's arterial oxygen saturation can be measured by taking a ratio of ratios (ROR) of the two signals—that is, by taking a ratio of the alternating component (AC) of each signal to its direct, non-alternating component (DC) and dividing the red ratio by the infrared ratio.

In a video-based system, the Red/Green/Blue pixels or regions detected by the camera provide three light intensity signals that potentially can be used in a similar ratio of ratios calculation, such as by dividing the ratios of any two of the three signals. However, many standard video cameras do not detect light in the infrared wavelengths. Moreover, for many video cameras, the wavelengths of light detected in each of the Red, Green, and Blue components overlap. For example, the video camera 214 (see FIG. 2A) may include an image sensor with broad spectrum red, green, and blue detectors. The wavelengths detected by these detectors overlap, and are not chosen specifically for their relative absorption by oxygenated hemoglobin. As a result, measuring a ratio of ratios from two of the three signals does not provide an absolute, calibrated SpO2 value. However, such a ratio of ratios can be used to track the trend of the patient's actual SpO2 value.

Figure 6B:
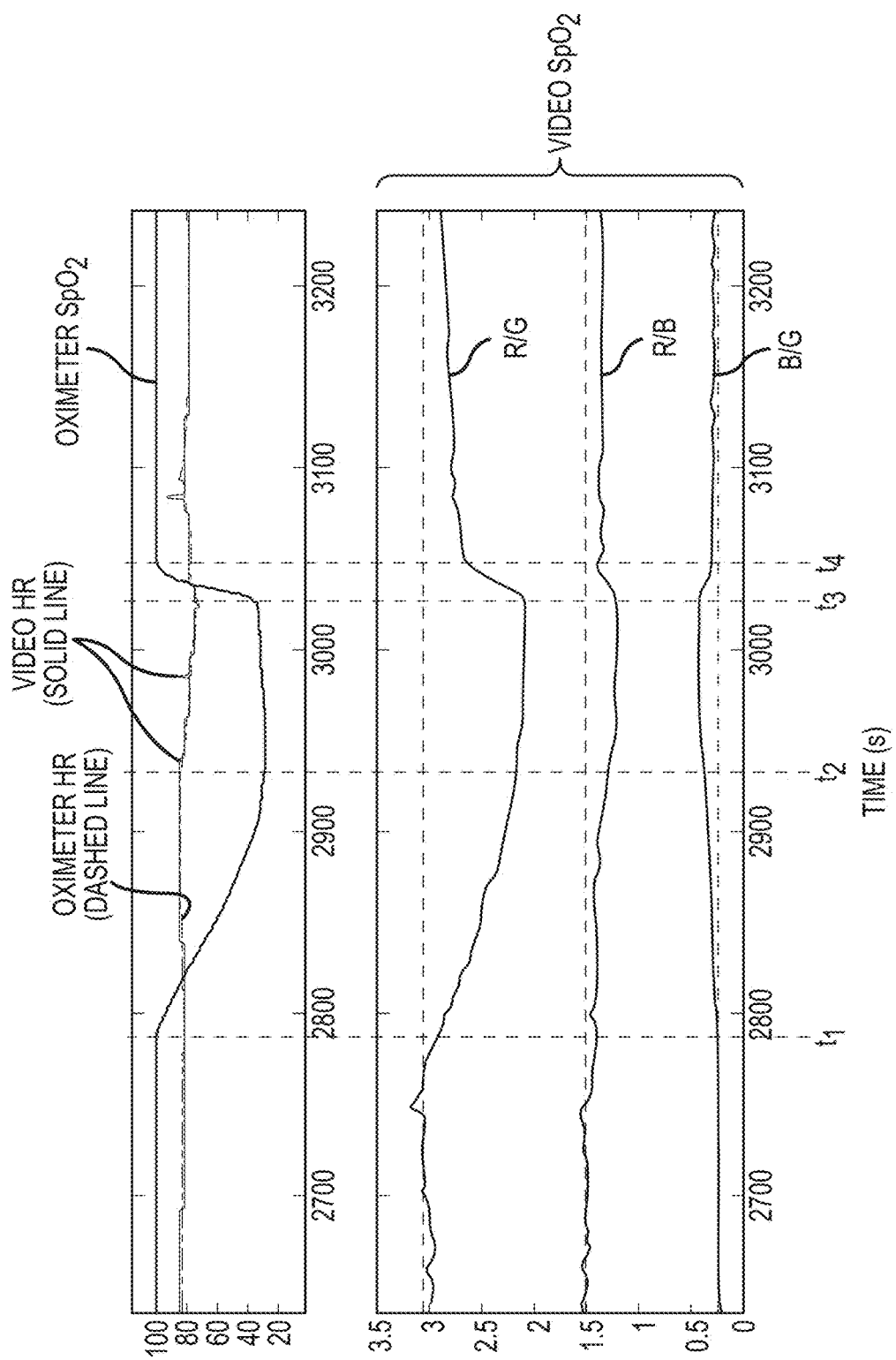
FIG. 6B is a chart of contact-oximeter-based and video-based vital signs (heart rate and SpO2) over time according to an embodiment of the invention.

Such a trend is shown in FIG. 6B. The top plot in FIG. 6B shows an SpO2 value from a calibrated, contact-based pulse oximeter. It also shows two heart rate signals, one taken from the same pulse oximeter and the other from a video signal. It is readily apparent that the video-based heart rate signal tracks the oximeter-based heart rate signal very closely, providing good absolute correlation.

The bottom plot in FIG. 6B shows three different SpO2 values from a video signal, one for each pair of signals. The top trace is from a ratio of ratios calculation of the Red and Green signals, the middle is the Red and Blue signals, and the bottom is the Green and Blue signals. These three traces can be compared with the calibrated SpO2 value plotted above, from the conventional contact pulse oximeter. It is clear from FIG. 6B that all three traces correlate with the calibrated SpO2 plot, in that they trend up or down in proportion to the calibrated SpO2 plot. However the absolute values (shown in the y-axes in FIG. 6B) of the video-based SpO2 traces do not match the calibrated SpO2 value itself. The calibration of the SvidO2 against SpO2 may be performed by linear regression, whereby the coefficients of the regression model are applied to the SvidO2 to estimate the absolute SpO2 values.

In an embodiment, the video-based SpO2 measurement is used as a trend indicator, rather than as a measurement of an accurate SpO2 numerical value. For example, it is apparent from the Blue-Red trace that the SpO2 value remains stable until time t1, begins to change at time t1, decreases until time t2, remains stable at low oxygenation until time t3, increases again until time t4, and thereafter remains stable again. The Blue-Red trace can thus be used as a trend indicator, to provide an alert that the patient's SpO2 value is changing, and can even indicate whether the SpO2 value is increasing or decreasing, and an indication of the rate of increase or decrease. This information can be used to provide an early warning to a caregiver that the patient needs attention, such as by attaching a traditional contact-based pulse oximeter to obtain a numerically accurate reading of the patient's SpO2 value which can be used to determine a diagnosis or treatment.

In another embodiment, the SpO2 value measured from a pair of the Red/Green/Blue pixel streams is calibrated to an accurate numerical value. Calibration can be done by comparing the video-based SpO2 value to the value from a reference contact-based oximeter, to identify an offset between them. This offset is used to determine a scaling factor that is applied to the ROR calculation from the video signal. For example, the scaling factor can be a coefficient multiplied to the video ROR, or an offset added or subtracted from the video SpO2, or both. This offset and/or coefficient can be used until the next recalibration. Recalibration can be done when a set time has expired, or when the video SpO2 trend shows a marked change in SpO2.

Figure 7:
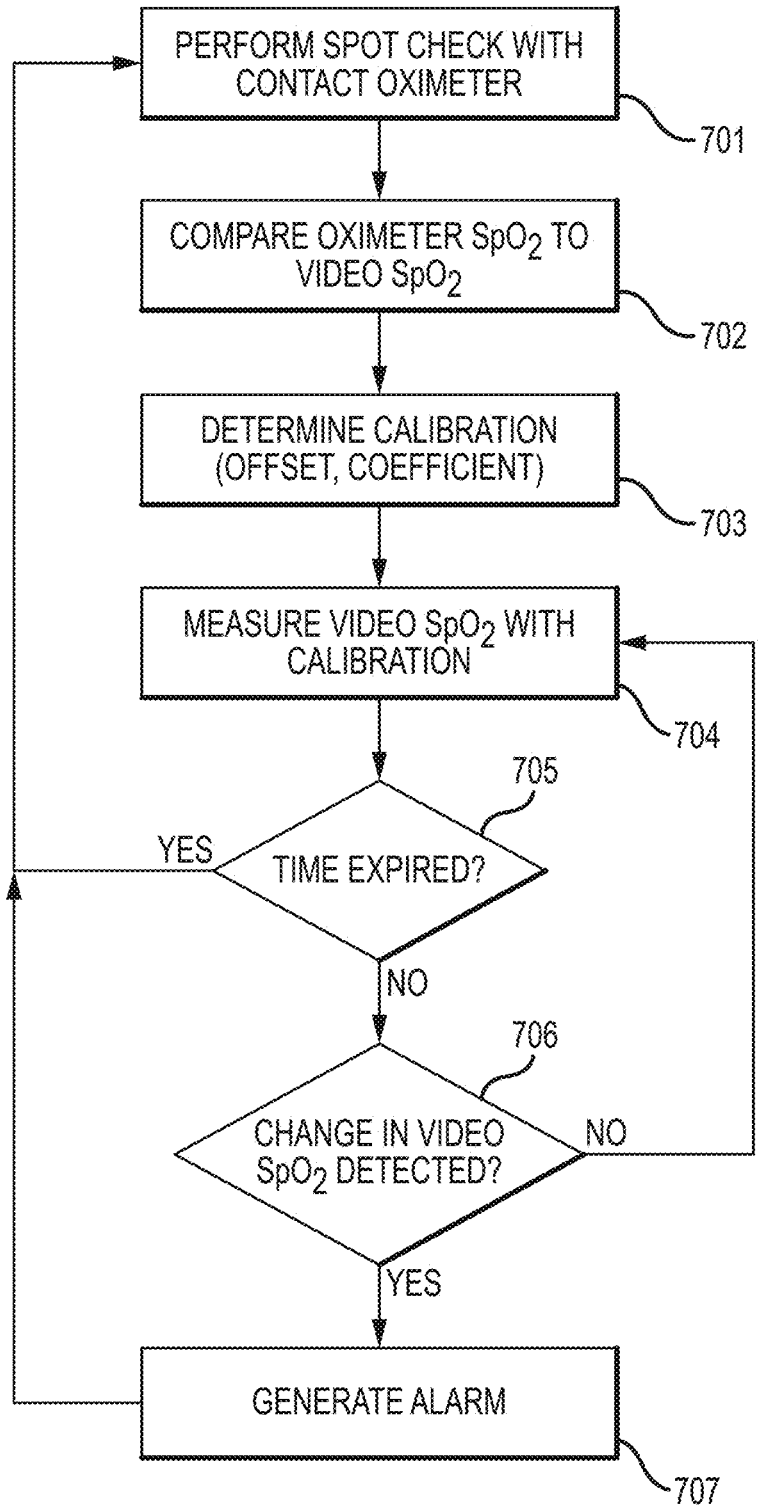
FIG. 7 is a flowchart of a method of calibrating video-based pulse oximetry according to an embodiment of the invention.

FIG. 7 shows a method of calibrating a video-based SpO2 measurement, according to an embodiment of the invention. The method includes performing a spot check with a contact oximeter at 701, comparing the oximeter SpO2 to the video SpO2 (also called $S_{vid}O2$) at 702, and determining the calibration between the two values (such as an offset, scaling factor, and/or coefficient) at 703. The method then includes measuring SpO2 from the video signal with the calibration at 704. At 705, a timer is used to prompt re-calibration. For example, the timer may be set to expire in 15 minutes, or one hour, or two hours, or other time durations desired by the caregiver. If the time has expired, the method returns to 701; if not, the method continues to 706, where the video SpO2 value is compared to a threshold to identify changes. If the video SpO2 value crosses the threshold, the method includes sounding an alarm (such as an audible sound and/or a visible alert) at 707, and prompting re-calibration at 701. If not, the method returns to continue measuring at 704. The threshold used to detect a change at 706 can be set by the caregiver to identify changes in video SpO2 that may indicate a clinically significant change in the patient's physiology, for further diagnosis or treatment.

When calibration or re-calibration is not available, the monitor may continue to calculate video SpO2 to identify trends. The trend from the video SpO2 may be used to trigger an alarm when the trend shows that SpO2 is rapidly changing or has crossed an alarm threshold. Clinically relevant patterns (such as repeated desaturations) may also be detected from the video SpO2 signal, between or in the absence of re-calibrations.

Figure 8:
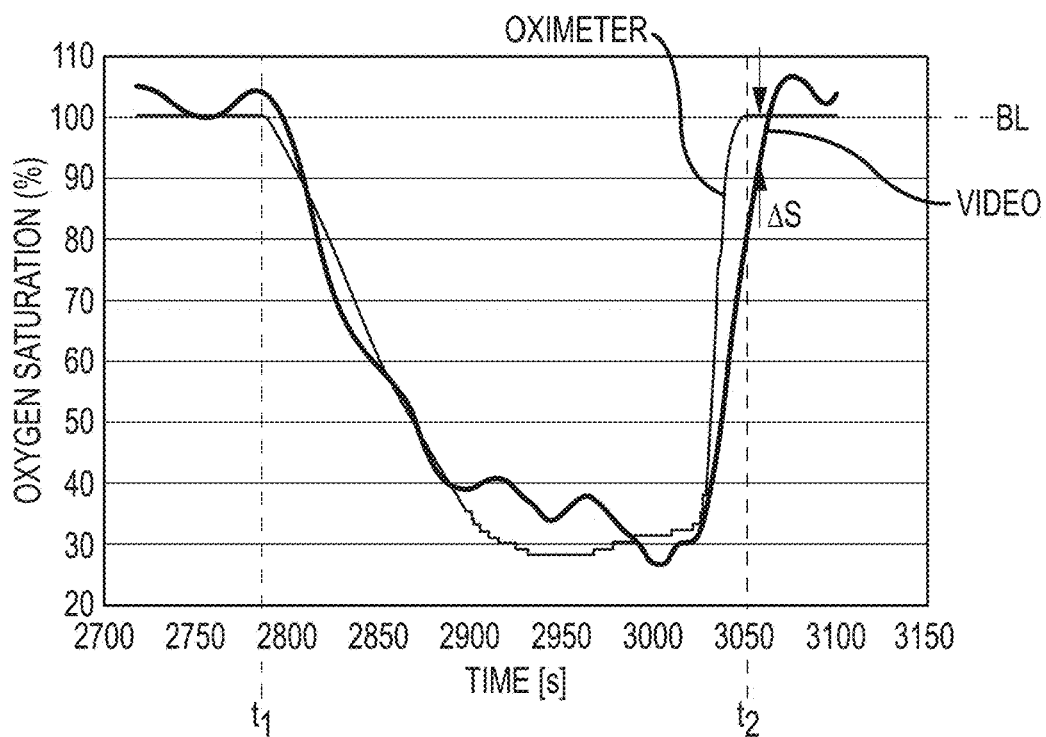
FIG. 8 is a chart of video-based and contact-based measurements of arterial oxygen saturation over time, including a desaturation event, according to an embodiment of the invention.

When the video-based SpO2 value is calibrated to an accurate measure of oxygen saturation, it can be tracked from there to measure the patient's actual SpO2 value. An example of this is shown in FIG. 8, which plots two SpO2 values, one from a traditional contact-based pulse oximeter, and the other from a calibrated video-based pulse oximeter. The video-based SpO2 value in this example is taken from the Red and Green signals, and then calibrated with an absolute SpO2 value as described above. Once calibrated, it is clear from FIG. 8 that the video-based SpO2 value tracks the patient's absolute SpO2 value closely. The data presented in FIG. 8 was collected during a clinically-relevant desaturation event in which the subject's oxygen saturation dipped and then recovered.

Though the video-based SpO2 measurement can be calibrated from a contact-based pulse oximeter, the video-based SpO2 measurement may exhibit different behavior over time, as compared to a traditional contact-based oximeter. These differences may arise due to the differences in filtering characteristics between the contact-based oximeter and video camera, and/or differences in the light waveforms detected by a remote video as compared to a contact-based sensor, and/or other factors. As an example, the light detected by a remote video camera may be reflected from a shallower depth within the patient's tissue, as compared to contact-based oximetry, which utilizes a contact sensor to emit light directly into the patient's tissue. This difference in the light signal can cause the morphology of the video-detected waveform to differ from a contact-based waveform. As another example, the light detected by a remote video camera is more susceptible to ambient light noise incident on the surface of the region being monitored.

As a result, the SpO2 measurement from the video-detected waveform exhibits some differences from the contact-based SpO2 measurement, even when the two are first calibrated together. An example of this behavior is evident in FIG. 8. Between times t1 and t2, the subject's oxygen saturation drops and then recovers to a baseline level BL. Both waveforms track this trend, but the video-based measurement is slower than the contact-based measurement to return to baseline. The result is a difference, labeled ΔS (delta saturation) between the two measurements. Because this behavior of the video-based measurement is known, it can be corrected for, by adjusting the value upward during an increasing trend. This adjustment can be tailored based on empirical data. An adjustment may be made by finding the relationship (mapping) between the video-based SpO2 and the contact-based (oximeter) SpO2. This relationship may then be coded within the video system to mimic the oximeter-based SpO2.

In an embodiment, the video-based non-contact monitoring system identifies acute hypoxia in monitored patients, by identifying episodes of decreased oxygen saturation. The system provides continuous monitoring of vital signs such as video-based SpO2, rather than discrete, periodic spot-check readings. This continuous monitoring, via either trending or calibrated video SpO2, enables the system to identify clinical conditions such as acute hypoxia, and repeated interruptions in airflow.

In an embodiment, a monitoring system is programmed to take certain steps including activating alarms or messages when a suitable physiologic signal is not ascertainable in the field of view. For example, in an embodiment, a processor acquires a physiologic signal (as described above), and determines a physiologic parameter from the signal. However the signal may be lost when the patient moves out of the field of view, or moves in such a way that a physiologic region (such as exposed skin) is not visible, or moves too quickly for accurate tracking. The signal may also be lost if another person or item moves into the field of view and blocks the camera's view of the patient, or if the room becomes too dark (such as if room lights are turned off at night). In any of these or similar situations, the processor starts a timer counting down, and holds the previous value of the calculated physiologic parameter. After a short duration, the processor may send an alert message to be displayed on a screen or otherwise notified to a clinician, to indicate that the signal has been lost and the parameter value is held frozen. If the timer expires, the processor can then sound an alarm or other notification, such as an escalated message or indicator, and remove the frozen physiologic parameter value (or otherwise indicate that it is a previous value, no longer being updated). This can be a system-level alarm or notification, which indicates a problem with the signal acquisition, as distinguished from a physiologic alarm (that would indicate a physiologic parameter of the patient crossing an alarm threshold). This alarm or notification can be a message stating that the room lights have been turned off, or the patient has exited the field of view, or the patient is obscured in the field of view, or the patient is moving, or other applicable circumstance.

This message can be displayed at a remote station (such as a nursing station at a hospital) or on a remote, wireless device (such as a smartphone, tablet, or computer). Additionally, at a central monitoring station (such as a nursing station at a hospital), where display screens display information about multiple different patients, the video-based monitoring system can alert the central station to highlight an individual patient. For example, the remote monitoring system can send an alert or flag based on a change in condition (a system-level alarm, a physiologic alarm, an activity level of the patient, etc.), and the central station can then enlarge the video stream from that particular camera. This enables the caregivers at the station to quickly assess the situation in the room and determine if urgent action is needed.

In an embodiment, the processor identifies or is informed that a clinician or caregiver is interacting with the patient, and the processor temporarily halts dynamic tracking of the intensity signal and/or temporarily halts calculation of a physiologic parameter from the intensity signal. This step is taken because such interaction interferes with the camera's view, rendering the light intensity signals more noisy and less reliable. When the interaction is finished, the processor resumes its remote monitoring of the patient.

Ambient Light

Figure 11:
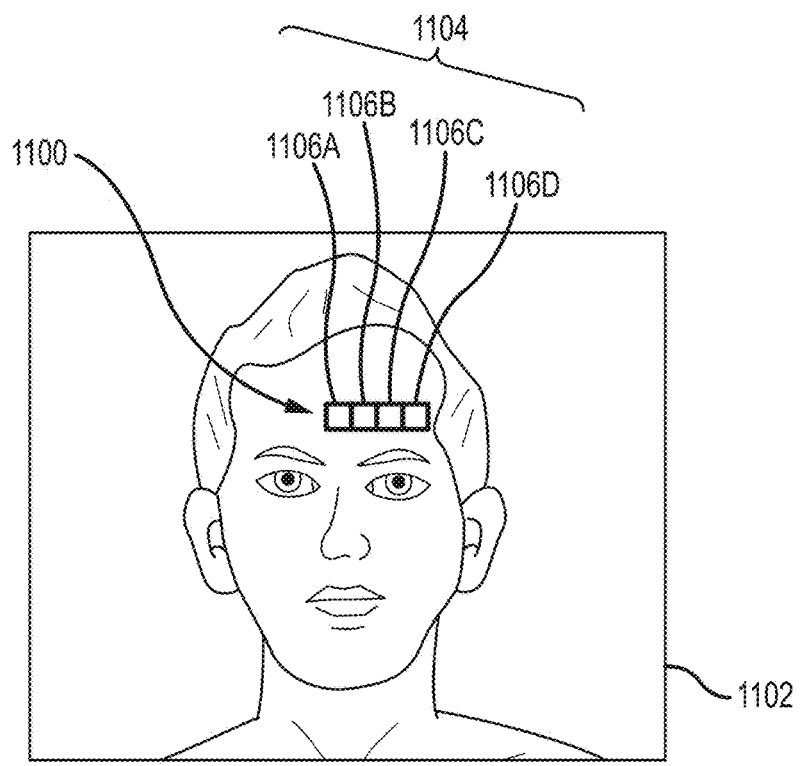
FIG. 11 depicts a patient in an image frame according to an embodiment of the invention.

As mentioned previously, changes in ambient light in the camera's field of view can obscure the subtle variations in the detected pixel streams that are attributable to the patient's physiology. In an embodiment of the invention, a video-based monitoring system includes a calibration strip that can be used to identify and correct for these changes in ambient light. A calibration strip 1100 according to an embodiment is shown in FIG. 11. The calibration strip 1100 is sized to fit on the patient (such as along the patient's forehead) and within the field of view 1102 of the camera. In an embodiment, the calibration strip 1100 includes a scale which displays a range of values for measurement, such as a greyscale with two or more grey or white hues; or a color map with two or more different colors. The scale can include a continuous spectrum of varying intensity and/or color, or it can include a set of discrete areas each with a different color and/or intensity. In one embodiment, the color map includes one or more known skin tone colors, which are then compared to exposed skin of the patient to identify an approximation of the patient's skin tone, which can then be used to adjust the exposure settings if the camera based on the light intensity of the skin. These values may vary along one (e.g. longitudinal) or two dimensions of the calibration strip. For example, the calibration strip 1100 shown in FIG. 11 includes a grid 1104 with four different discrete regions 1106A, 1106B, 1106C, and 1106D. Each region displays a different intensity and/or color. The colors have a known chromatic value, which allow for the colors in the captured video image to be color balanced to make corrections. Another example is a strip with a grey square or other shape. The intensity of the patch or portions of the patch (such as a grey square) identified in the video image can be used to adjust the exposure settings on the camera. In an embodiment, the calibration strip has a matte finish to reduce reflected light.

In an embodiment, a calibration strip includes spaces that are Red, Green, Blue, and white. This strip provides a reference for color balancing the region of interest on the patient. For example, if the white space from the calibration strip appears with a green hue on the image, then the region of interest can be color balanced to remove the green skew. This can be particularly helpful for SpO2 measurements.

Figure 9:
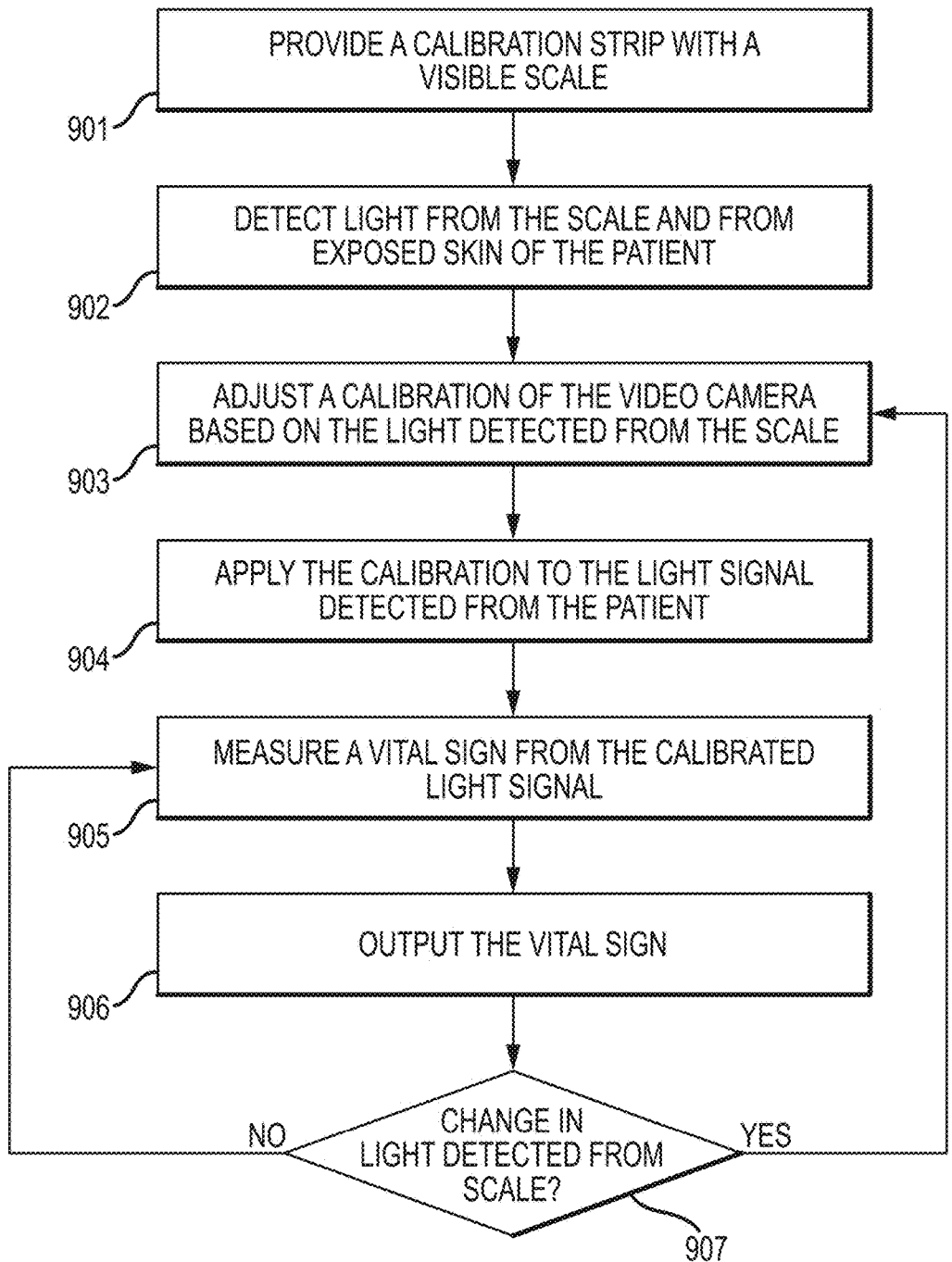
FIG. 9 is a flowchart of a method for calibrating a video camera according to an embodiment of the invention.

FIG. 9 shows an embodiment of a video-based method of measuring a patient's vital sign. The method includes providing a calibration strip comprising a substrate with a visible scale for viewing by the video camera in the same field of view as the patient, at 901. The method includes detecting, by the video camera, a first light signal reflected from the scale and a second light signal reflected from exposed skin of the patient at 902, and adjusting a calibration of the video camera based on a measurement of the first light signal at 903. The method includes applying the calibration to the second light signal at 904, measuring a vital sign of the patient from the calibrated second light signal at 905, and outputting the measured vital sign at 906 for further processing or display. The scale may be a greyscale or a color map. The measurement of the first light signal can be a measurement of an intensity of the light reflected from the scale, such as a portion of the color map or the greyscale.

The method includes monitoring the measured intensity to detect changes in ambient lighting in the room at 907. For example, at a later time, the system measures a second intensity that differs from the first intensity by a defined amount (such as an amount exceeding a threshold, to avoid excessive adjustments), such as a sudden increase or decrease in intensity due to room lights being turned on or off. If this change meets the defined amount or threshold (or other criteria), the method passes back to 903 to adjust the calibration based on the second intensity, such as by adjusting a coefficient in proportion to the defined amount or the new measured intensity. The coefficient is applied to the light intensity signal, to re-normalize the signal to the second intensity. The coefficient is applied by the camera in generating the red, green, and blue pixel signals. Otherwise, the method returns to 905 to continue monitoring. This method enables the red, green, and blue signals to be normalized to reference values, to better identify the physiologic signals even in differing light conditions. This normalization also enables two different cameras, monitoring two different patients, to be adjusted to the same reference color or brightness values, so that the vital signs or other measurements from the light signals can be compared to each other, without skew due to different camera hardware or light conditions.

In an embodiment, the scale on the patient includes a color map with a plurality of colors, and the measurement of the first light signal is a measurement of a color value of one of the plurality of colors. Then, the calibration is adjusted by comparing the color value to a reference color value and identifying a difference. Baseline color values from the scale can also be stored at a first time, and then the calibration can be adjusted later based on comparisons of new measurements (of light from the scale) to the stored baseline color values, such as when the new measurement deviates from the baseline by a defined amount. When a second video camera is used in the same room, the second camera can be calibrated based on the same reference, baseline, or other values used for the first camera.

In an embodiment, a calibration strip includes a white space, and the system measures the brightness of that white space in the image. This brightness indicates the amount of light hitting that region. The white space is monitored for changes in brightness, which may indicate a passing shadow or change in lighting conditions, including changes due to movements outside the field of view that change the amount of light reflected onto the region of interest. The color signals from the region of interest can then be filtered according to the changes in brightness, to continue tracking SpO2 (or another vital sign) during transient changes in lighting, such as due to motion in the room. This can be done, for example, with an adaptive filter based on the reference signal from measurement of the white space. Average light intensity within the identified white space can be used as a baseline to compensate non-physiological changes in the sampling regions. Alternatively, the color signals and/or vital sign measurements can simply be discarded during these transient changes.

In an embodiment, a calibration strip includes a graphic with high contrast, such as a dark dot, cross or circle on a white space, or a grid of colors. The system can track this high contrast shape to track movement of the patient. For example, the system can track the position and orientation of the high contrast graphic, and can generate a motion signal that tracks that movement. The motion signal may be a transform that maps the movement of the graphic. The same transform is applied to the region of interest in the patient, to track the movement of that region. If the transform reveals that the region of interest has exited the field of view, then a new region of interest is identified, based on the desired vital sign. Further, limits can be placed on the allowable rate of motion (such as angular rotation limits), and if the limits are exceeded, the color signals and/or measurements from the region of interest can be discarded.

Figure 12:
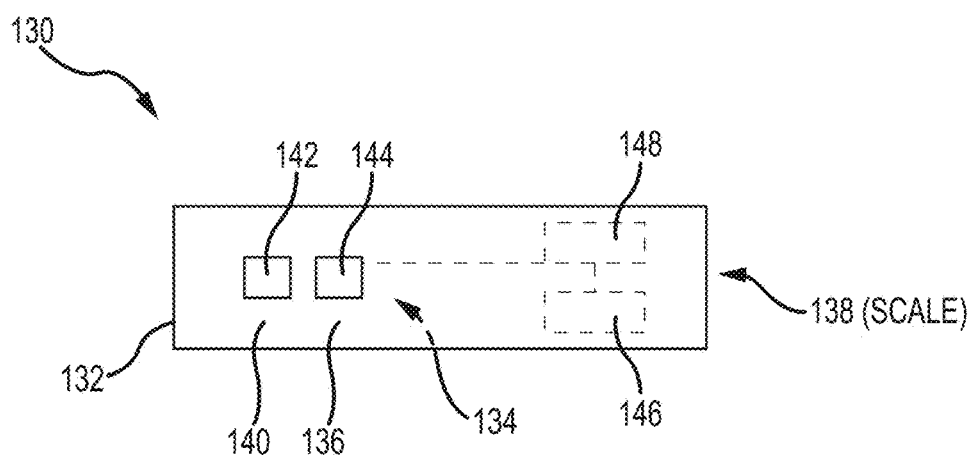
FIG. 12 is a bottom view of a calibration strip according to an embodiment of the invention.

In another embodiment, the calibration strip includes light emitters that emit light of selected wavelengths into the patient, but without the detector of traditional contact-based oximetry sensors, and without any transmitter for transmitting detected light. For example, a calibration strip 130 according to another embodiment is shown in FIG. 12. In this embodiment, the calibration strip 130 includes an adhesive patch 132 that is sized to fit within the field of view of a non-contact camera, such as on the patient's skin. The patch 132 includes a top surface 134 that faces away from the patient, opposite a bottom surface 136 that faces toward and contacts the patient. The top surface 134 carries a scale or graphic 138. The bottom surface carries an adhesive 140 that removably adheres to a patient's skin. The patch 132 also includes two emitters 142, 144 coupled to a battery 146 and a microprocessor 148. When the patch is placed on a patient's skin, the processor 148 drives the emitters 142, 144 to emit light sequentially into the patient's skin. The processor drives the emitters in a four-part sequence, in which the first emitter is on, then both emitters are dark, then the second emitter is on, and then both emitters are dark. This sequence is repeated at high frequency, such as 15-30 Hz.

However, notably, the patch 132 does not include a photodetector or any type of transmitter. Rather, the detector is a non-contact video camera viewing the patient, as described above. The video camera records image frames that include at least the portion of the patient's skin surrounding or near the patch 132. Light from the emitters travels through the patient's tissue and out through this portion of the patient's skin, such that it can be detected by the video camera. This system is a hybrid approach, employing contact-based emitters and a non-contact, remote detector. The system benefits from having dedicated light emitters at chosen wavelengths (for example, a narrow range of red and green wavelengths), creating a stronger physiologic signal in the detected image frames, while at the same time avoiding the drawbacks of a tethered sensor system. The patch 132 does not have any cables or wires connecting it to a monitor, nor any wireless communication. The patch 132 does not require any communication at all between itself and the camera or the monitor (such as the camera 214 and monitor 224 in FIG. 2A). As a result, the patch can omit components such as a wireless transmitter or receiver and supporting components such as batteries for those devices. The processor 148 carried by the patch can operate at very low power, operating only to drive the emitters 142, 144 and not to process or transmit any detected signal. The processor and emitters can be powered by a small battery 146. The patch is also small and lightweight, making it relatively comfortable for the patient to wear, and it does not interfere with the patient's mobility. The camera may begin monitoring the patient's vital signs automatically when it detects the emitted light, or it may be turned on by a caregiver.

It should be noted that the scale 138 shown in FIG. 12 is optional. In an embodiment, the patch 132 omits the scale 138 on the top surface, and is not used as a calibration strip. In another embodiment, the patch 132 includes a single color on the top surface, such as white, for use in measuring brightness and detecting passing shadows.

Independent Component Analysis

Due to the exposure of the camera detector to significant ambient light noise, the video-based system employs new approaches to filter the ambient light noise and identify the physiologic signal from which the patient's vital sign can be measured. An approach for filtering according to an embodiment of the invention is demonstrated in FIGS. 13-16. In this embodiment, independent component analysis (ICA) is used to decompose the Red, Green, and Blue pixel streams into individual components. ICA is a filtering method that, based on certain assumptions, separates input signals (also called source signals) into separate, independent components that are mixed together in the input signals. The ICA method is described in detail in the following paper: Hyvärinen, A., & Oja, E. (2000). Independent component analysis: algorithms and applications. Neural networks, 13(4), 411-430.

Figure 13:
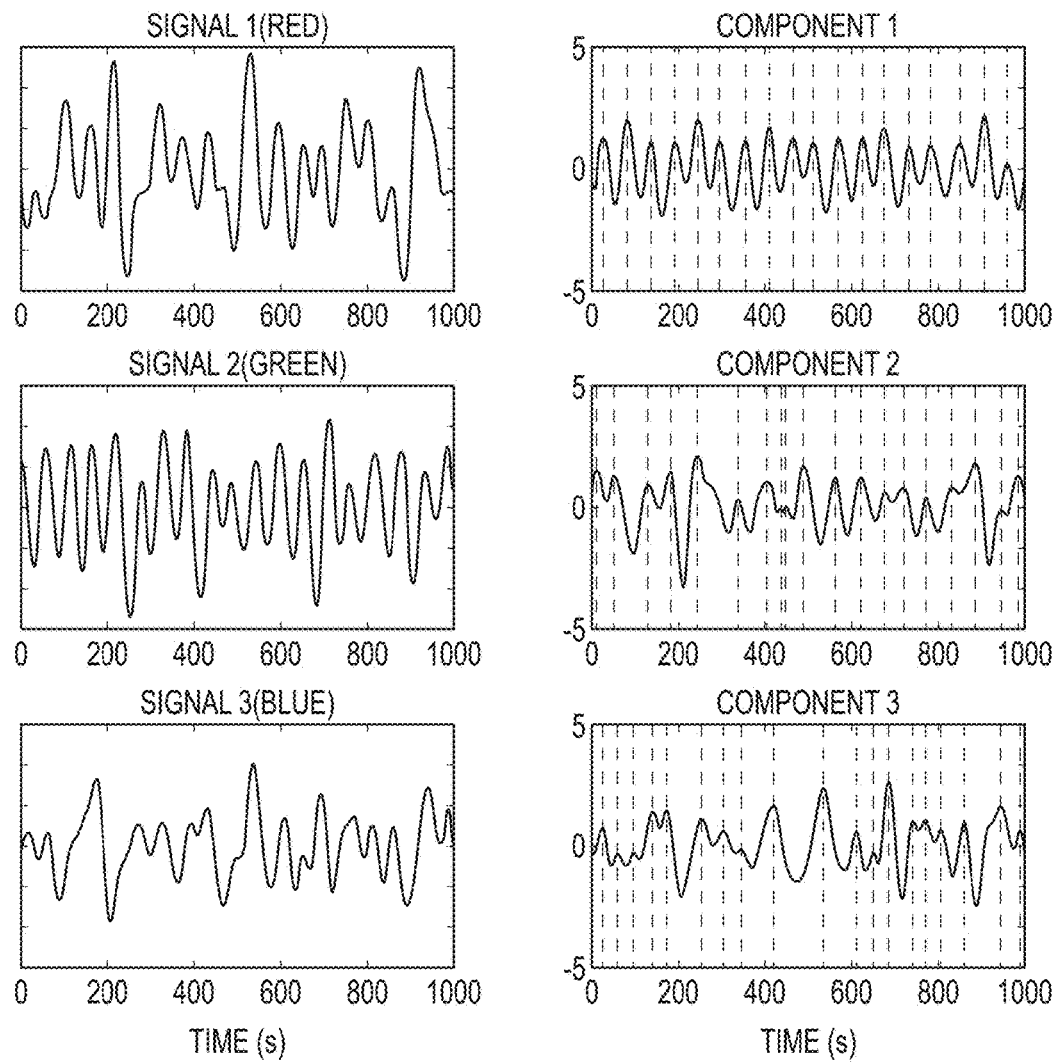
FIG. 13 is a set of charts showing three source signals and three independent component signals according to an embodiment of the invention.

In the context of video-based monitoring, the source signals are the Red, Green, and Blue pixel streams, and the independent components are the heart rate and the noise. Referring to FIG. 13, the source signals are shown in the three plots on the left, with the Red pixel stream on top, Green in the middle, and Blue on the bottom. These source signals are decomposed via an ICA method into three separate, independent components, shown on the three plots on the right (labeled Component 1, Component 2, and Component 3).

As shown in FIG. 13, Component 1 exhibits a repeating pattern of modulations at a relatively steady frequency. Component 1 is constructed from the portions of the source signals that modulate at that frequency. In this case, the frequency of the modulations in Component 1 represents the heart rate of the patient. The contributions of the patient's heart rate to each source signal have been pulled together and combined into the waveform of Component 1, creating a waveform that identifies the heart rate more clearly than any single source signal did. The patient's heart rate can be measured from the primary frequency of Component 1.

Still referring to FIG. 13, Components 2 and 3 are relatively more erratic, and do not exhibit a clear primary frequency. These components capture the noise that corrupted the Red, Green, and Blue source signals. Each of the source signals represents a different mixture or combination of Components 1, 2, and 3.

By utilizing ICA to decompose the source signals, an underlying physiologic signal such as heart rate or respiration rate can be identified. As discussed above, different groups of pixels or regions can be selected to measure different vital signs, such as heart rate and respiration rate. FIG. 13 represents the source signals from a first group of pixels or regions that modulate with the patient's heart rate. These signals are decomposed via ICA to arrive at a relatively clean heart rate signal in Component 1. A different group of pixels or regions that modulate with respiration rate can also be decomposed via ICA to arrive at a relatively clean respiration rate signal. Another region may be decomposed via ICA to arrive a pulsatile signal that demonstrate perfusion status of the patient (such as by Delta POP or DPOP, by measuring the variations in amplitude of the pulses at the top and bottom of the baseline modulations). These vital signs may be measured from the same region or different regions.

In FIG. 13, Component 1 exhibits the most regular frequency, as shown by the plotted vertical lines. Vertical lines are placed in the plots of Components 1, 2, and 3 at each local maximum in the waveforms. The component with the most regularly spaced vertical lines is chosen as the component that represents the patient's heart rate. In FIG. 13, this is clearly Component 1.

Figure 14:
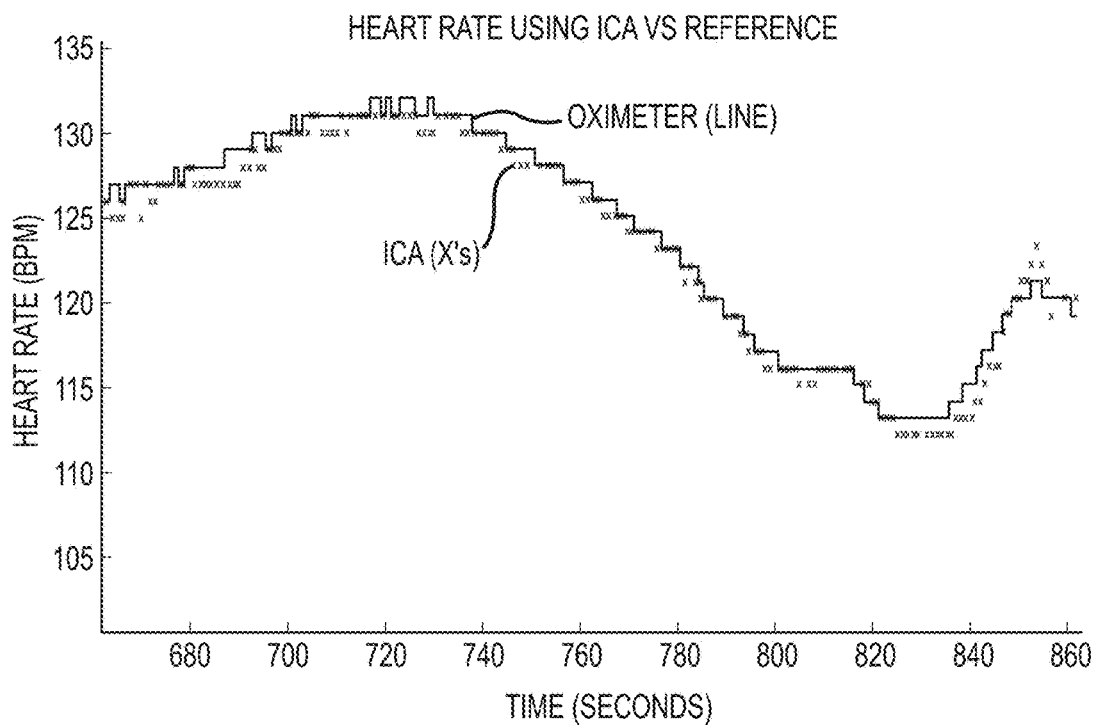
FIG. 14 is a chart of contact-oximeter-based and video-based ICA-derived heart rate values over time according to an embodiment of the invention.

FIG. 14 shows the results of an ICA method applied to a video stream to measure a patient's heart rate. The figure shows heart rate calculated by a traditional contact-based oximeter (solid line) as well as heart rate from an ICA filtered video stream (x's) from the same subject over the same time duration. The ICA-based heart rate shows good correlation with the traditional oximeter values.

Figure 15:
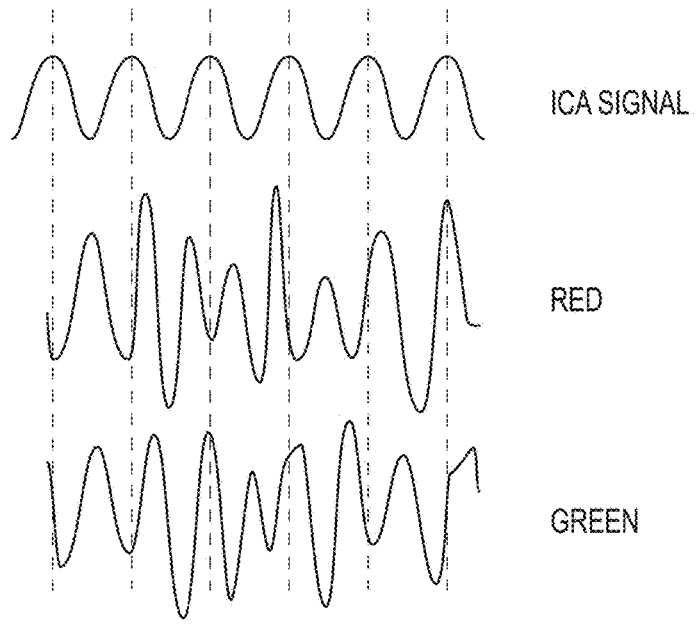
FIG. 15 is a schematic chart illustrating an independent component signal and two source signals, according to an embodiment of the invention.

After decomposing the source signals via ICA to identify a physiologic component (such as heart rate), that component can then be used to filter the original input signals, as shown in FIG. 15. FIG. 15 shows three traces—Component 1 on top, the Red source signal in the middle, and the Green source signal on the bottom. The vertical lines marked on the local maximums of Component 1 are projected onto the Red and Green pixel streams. The locations of these projections signify heart beats in the Red and Green pixel streams, even when these source signals are corrupted by noise. The ICA-derived heart rate signal of Component 1 can be used to identify the location of individual pulses in the source signals. The ICA technique finds the best representative pulse signal, which can then be used to locate pulses in the original Red and Green source signals.

Figure 16:
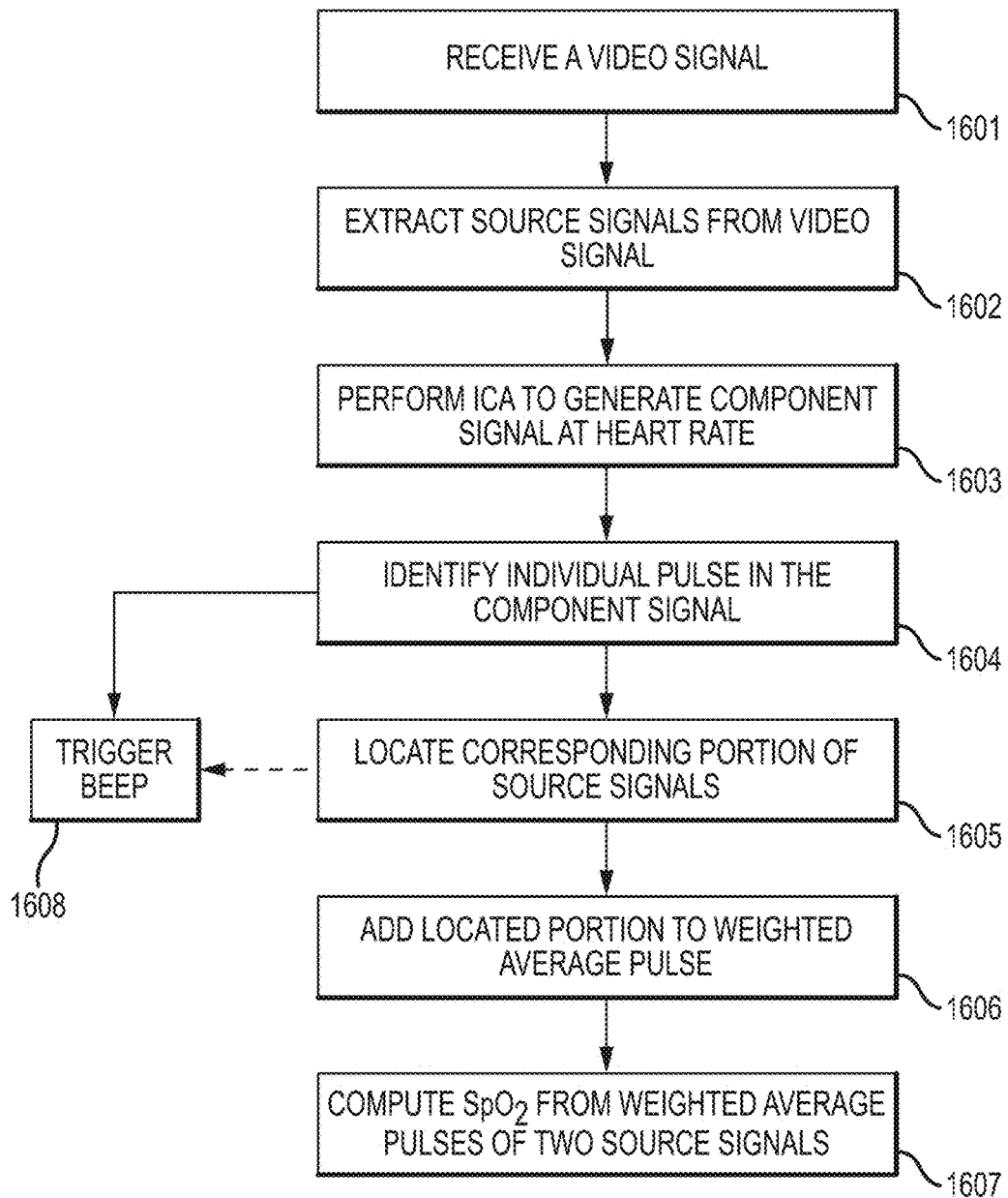
FIG. 16 is a flowchart illustrating a method for utilizing an independent component signal, according to an embodiment of the invention.

FIG. 16 depicts a flowchart of a method for measuring a vital sign of a patient with ICA, according to an embodiment. The method includes receiving a video signal from a video camera at 1601, and extracting from the video signal the source signals at 1602, such as time-varying red, green, and blue signals. The method includes performing ICA to generate a component signal having a primary frequency at the heart rate of the patient at 1603. Performing ICA involves decomposing at least two of the source signals into component signals, and selecting the component signal that exhibits the contribution of the patient's heart rate, as explained above. The method then includes identifying, in the selected component signal, an individual pulse representative of an individual heart beat at 1604. The method includes locating a corresponding portion of at least two of the red, green, and blue source signals at 1605. This can be done by determining a fiducial in the component signal (e.g. the maxima, minima, peak of the first derivative, etc.), and using this fiducial to identify a corresponding pulse or location in the source signals. Then, for each of those two source signals, the method includes adding the located portion to a weighted average pulse at 1606. This produces at least two of a red weighted average pulse, a blue weighted average pulse, and a green weighted average pulse. The method then includes measuring blood oxygen saturation of the patient from the weighted average pulses of the two signals at 1607 (such as by measuring an ROR, and computing SpO2 from the ROR). Heart rate can also be measured from the primary frequency of the component signal. The vital signs are output for further processing or display. In an embodiment, the method also includes triggering an audio beep at 1608 in synchrony with the individual pulse identified in the component signal, or in synchrony with the located corresponding portion of one or two of the color signals. This audio beep signifies the occurrence of a cardiac pulse. Instead of an audio beep, other audible or visual alerts may be triggered or displayed.

The ICA-derived pulsatile component signal is thus used as a trigger to inform the processor where to look in the original signals for relevant physiologic information. In turn, this trigger can be used to control an ensemble averaging method, in which sequential pulses are averaged with past pulses to create a smoother average cardiac pulse for each source signal. The ICA-derived trigger may also be passed to another medical device, such as a pulse oximeter, blood pressure monitor, or other monitor or processor, to inform that device that a cardiac pulse has been detected and the time or location of that pulse.

Noise Reduction

Another way to address noise is to identify non-physiologic peaks within the frequency domain, and remove those from the video signals. Two methods for identifying non-physiologic peaks are summarized here.

Figure 17A:
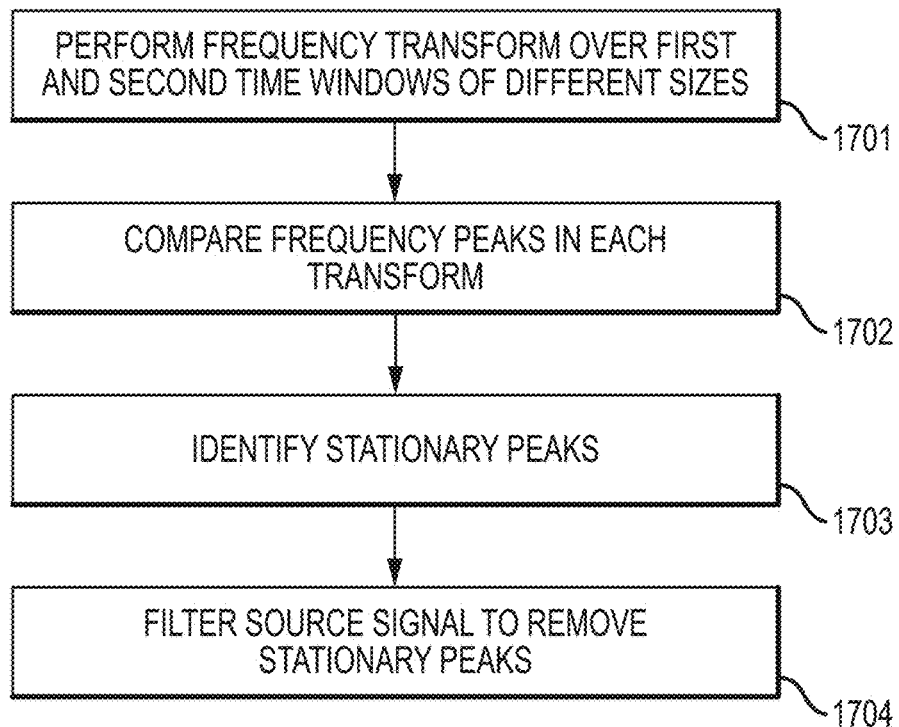
FIG. 17A is a flowchart illustrating a method for identifying non-physiologic frequencies according to an embodiment of the invention.

In one method, in the frequency domain, peaks are identified that remain stationary over a duration of time. Over a sufficient period of time (long enough for a few cycles of the vital sign—for example, 5-10 seconds for heart rate, or 20-30 seconds for respiration rate), peaks that remain stationary are likely to be non-physiological, such as peaks caused by aliasing from flickering room lights, while physiologic peaks should move and shift with the patient's state. A frequency transform such as an FFT can be performed over different time durations (such as different window sizes), and the frequencies that remain stationary, by appearing the same regardless of window size, are likely to be non-physiological. These identified frequencies can be removed by filtering. A flowchart illustrating this method is shown in FIG. 17A. In an embodiment, the method includes performing a frequency transform over first and second time windows of different sizes (different time durations) at 1701. The method includes comparing frequency peaks in the transforms at 1702, and identifying stationary frequency peaks at 1703. The method then includes filtering the video (source) signal(s) to remove the stationary frequency at 1704.

The number of window sizes, and their sizes relative to each other, can be varied to achieve a desired result. In an embodiment, two different window sizes are used, one 20 seconds in duration and the other 10 seconds in duration. In another embodiment, three window sizes are used, such as 20, 10, and 7 seconds each. This analysis can be done on each pixel signal individually, to remove identified frequencies from each signal, or it can be done on one signal and then the identified frequencies can be removed from all signals.

Figure 17B:
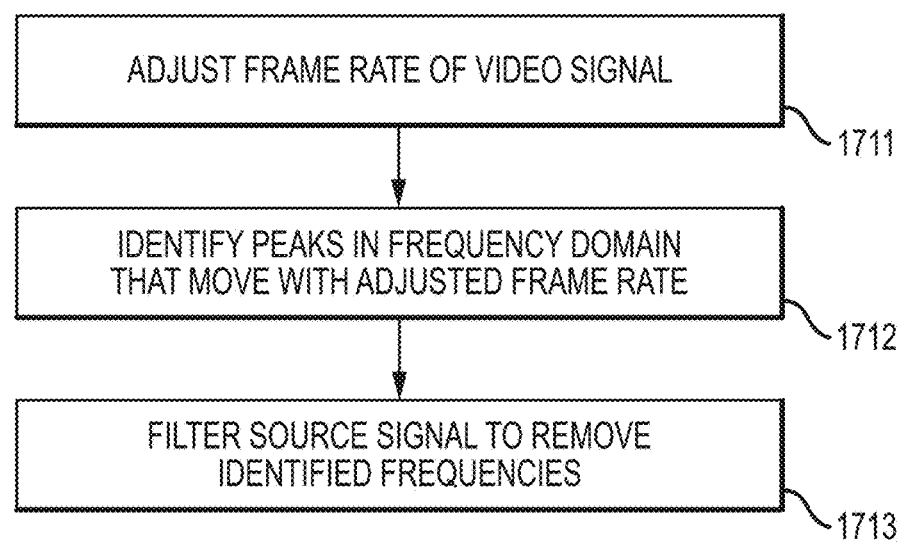
FIG. 17B is a flowchart illustrating a method for identifying non-physiologic frequencies according to an embodiment of the invention.

In another method, in the frequency domain, peaks are identified that move based on frame rate. Frequency peaks that move to another position or disappear when the video frame rate is adjusted may be taken as non-physiological, because physiologic modulations do not disappear or move instantaneously based on the video characteristics. In an embodiment, the frame rate sweeps at a constant sweep rate over a range of frequencies, or moves along a trajectory (such as a first frame rate for a first time duration, then a second frame rate for a second time duration, etc), and frequency peaks that move with that sweep or trajectory are considered non-physiological. Frequency peaks that move at the sweep rate are particularly suspect and can be removed. The speed of the sweep is faster than the expected variation of physiological parameters, such as heart rate. The frame rate can also change in random or pseudo-random ways, or through a set of non-stationary values, such as three or more discrete, different frame rates. Further, a frequency peak that remains stationary upon the change in frame rate is more likely to be physiological. A stationary peak can be identified, and a vital sign such as heart rate measured from this stationary peak. A flowchart illustrating this method is shown in FIG. 17B. In an embodiment, the method includes adjusting the frame rate of the video signal at 1711, and identifying peaks in the frequency domain that change or move with the adjusted frame rate at 1712. The method then includes filtering the source signal(s) to remove the identified frequency at 1713. In an embodiment, after the noise frequency has been identified, the frame rate can be fixed, until a later time when it is varied again to re-check for noise peaks.

The particular range of frame rates may depend on the capabilities of the camera hardware, and the light conditions. In an embodiment, the frame rate is varied from the highest well-exposed frame rate to lower frame rate, in one or more steps. An example range is 10-25 frames per second. In an embodiment, the period of time during which the frame rate is varied is longer than the expected period of the physiologic frequency (such as heart rate). The analysis described in FIGS. 17A and 17B can be done on each pixel signal individually, to remove identified frequencies from each signal, or it can be done on one signal and then the identified frequencies can be removed from all pixel signals.

Optical Splitter

In another embodiment, an optical splitter is employed in order to obtain two light signals from a single camera. These two light signals encompass the same field of view, monitoring the same subject, over the same time period, but the two signals can be filtered differently to facilitate physiological measurements. The two signals are synchronized in time and field of view, and include the same noise components, so the same de-noising operations can be used on both signals. The optical splitter is a simpler solution than two separate cameras, and provides more information than a single camera.

Figure 18:
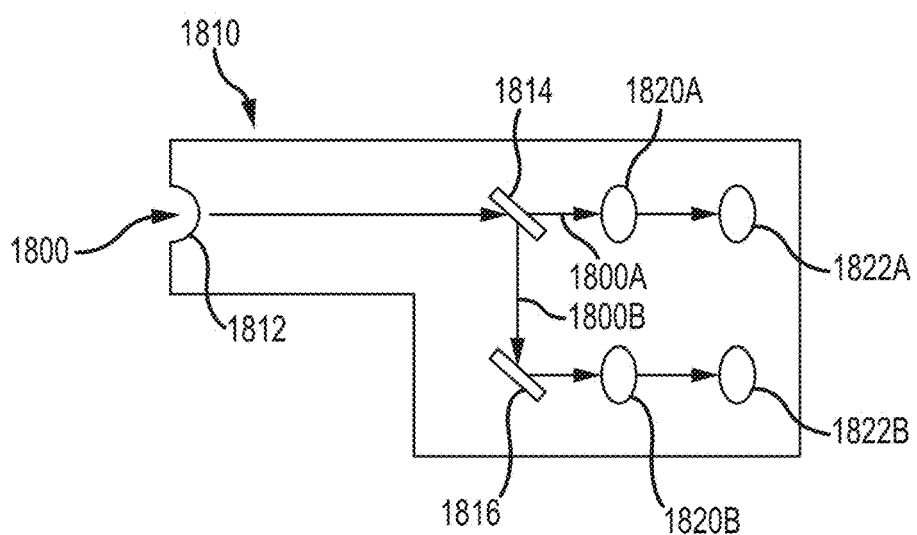
FIG. 18 is a schematic cut-away view of an optical splitter according to an embodiment of the invention.

An optical splitter 1810 according to an embodiment is shown in FIG. 18. The optical splitter 1810 is used to split a single light signal into two signals that pass through two different filters. The filters are chosen based on the physiologic signal that is to be measured. For example, for SpO2, the filters are chosen based on the extinction coefficients of hemoglobin. The two filters can pass visible and non-visible light, respectively, such as red and infrared light, or two narrow ranges of visible light. One filter may pass a narrow range of red wavelengths, and the second filter may pass a narrow range of green wavelengths, to mimic the red and infrared signals emitted by traditional contact pulse oximetry emitters. Referring to FIG. 18, the optical splitter includes an aperture 1812 that receives an incoming light signal 1800. The optical splitter includes a beam splitter 1814 positioned behind the aperture, in the path of the incoming light. The beam splitter 1814 divides the incoming light signal 1800 into two signals 1800A and 1800B. An example of a beam splitter is a dielectric mirror or a beam splitter cube, operating to split the incident light into two or more paths, in not necessarily equal proportions of strength. The separated light signal 1800B passes to a mirror 1816 that re-directs the light signal into the camera. Each light signal passes through a respective filter 1820A, 1820B. In the example of pulse oximetry, the filter 1820A is designed to pass a narrow range of red wavelengths, while the filter 1820B passes a narrow range of green wavelengths. The filtered light signals are received by respective detectors or light sensors 1822A, 1822B that register the resulting images. The result is two time-varying image signals filtered for specific wavelengths. Regions of interest are identified in the two signals for the calculation of vital signs such as SpO2, heart rate, and respiration rate, as described above. Absolute SpO2 can be calculated via a pre-calibrated look-up table, without the need for periodic re-calibration via oximeter spot check.

In another embodiment, additional splitters may be used to divide the light into more than two beams, to pass through additional filters chosen for other physiologic parameters. For example, an additional beam 1800N can be passed through a filter chosen for the measurement of total hemoglobin. In another example, a filter is chosen for carboxyhemoglobin, or for methemoglobin. In an embodiment, the filters are arranged on a rotating wheel, so that they are rotated in and out of the path of the light 1800, 1800A, or 1800B, to filter the incoming light as needed for the measurement of the physiologic parameters. This mechanical filter actuator can select appropriate filters to measure different parameters from the patient at different times.

Data

Figure 19:
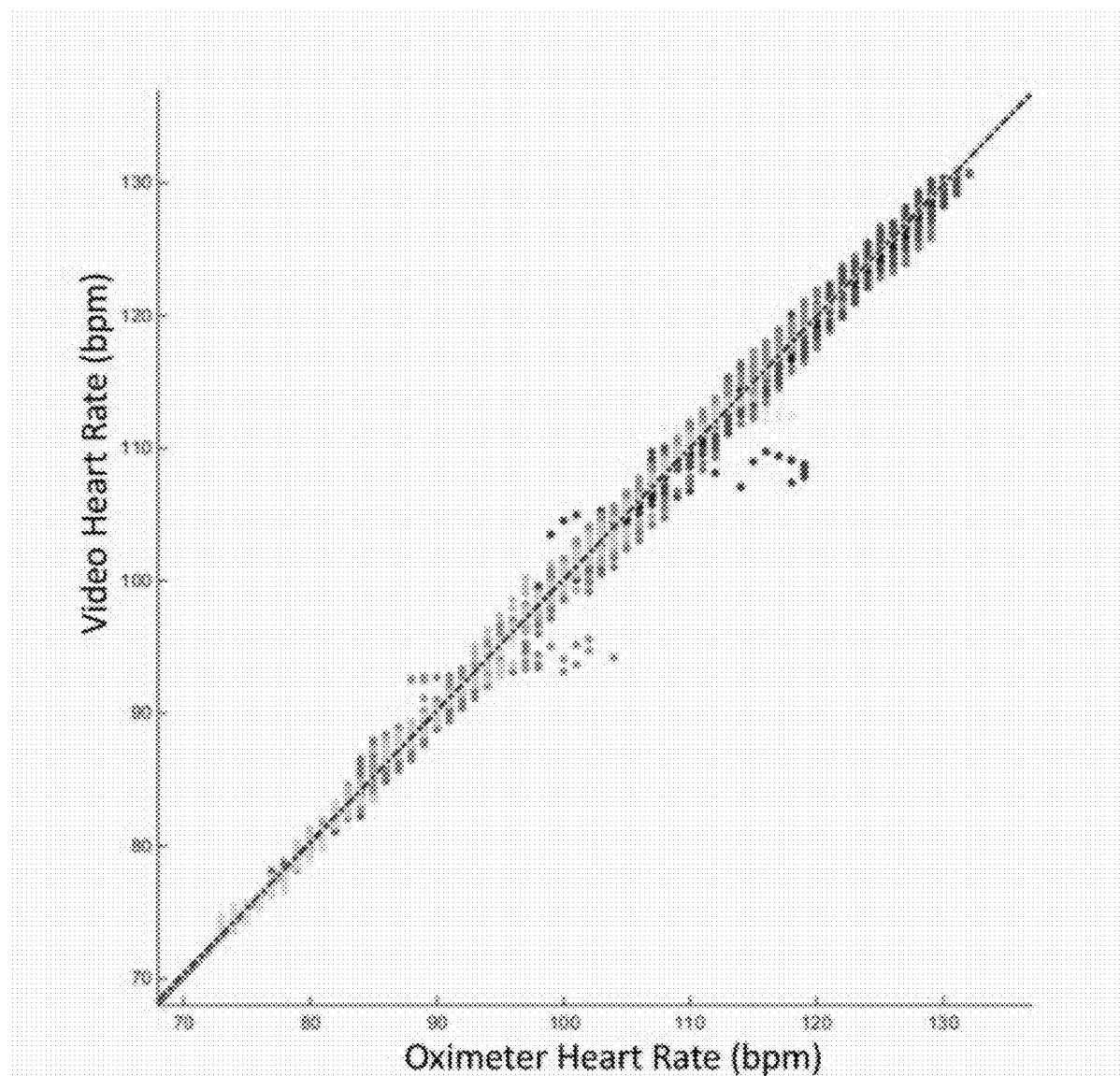
FIG. 19 is a scatter plot of video-calculated heart rate measurements against reference heart rate measurements, according to an embodiment of the invention.
Figure 20:
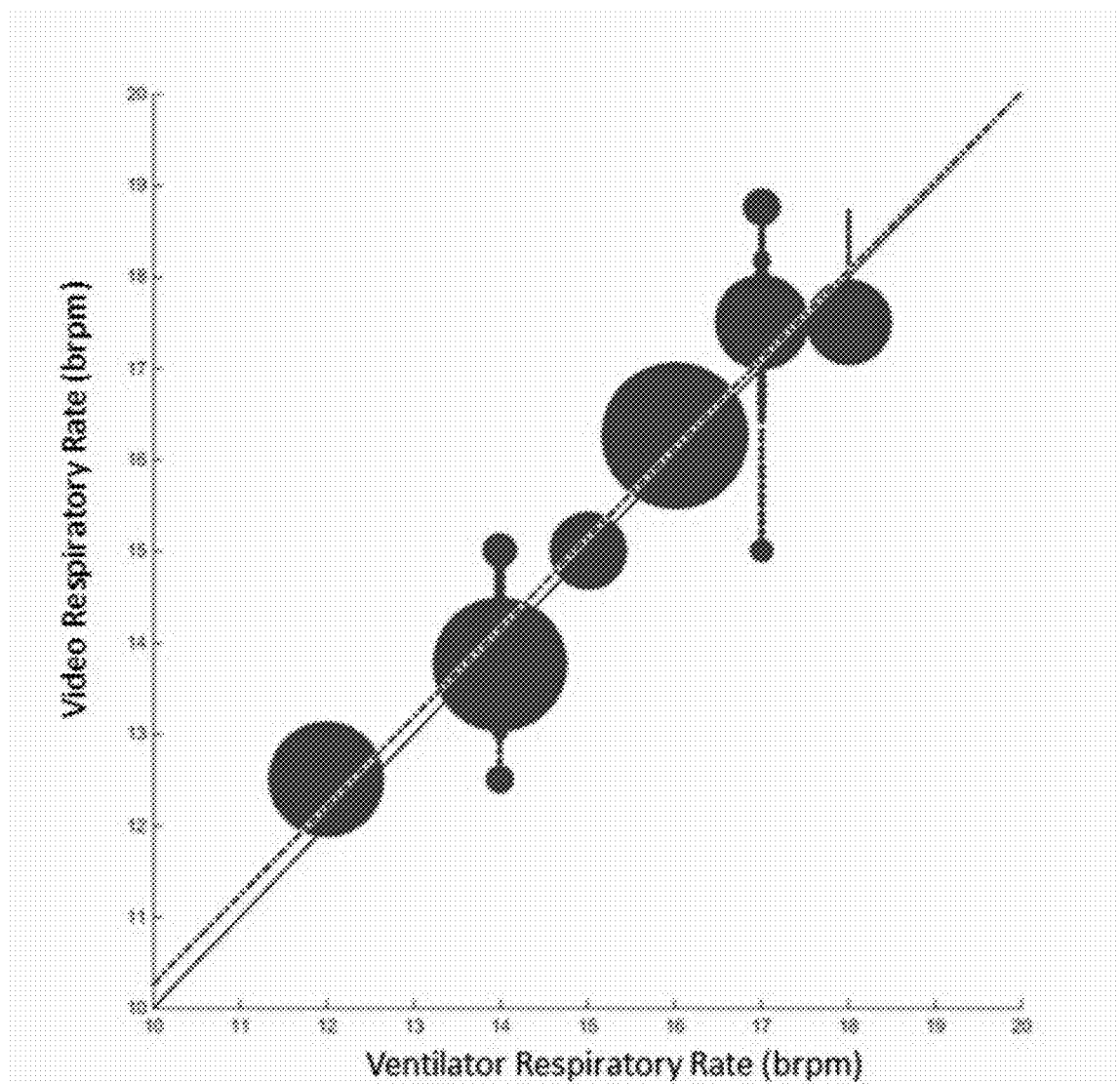
FIG. 20 is a scatter plot of video-based respiration rate measurements against reference respiratory rate measurements, according to an embodiment of the invention.
Figure 21:
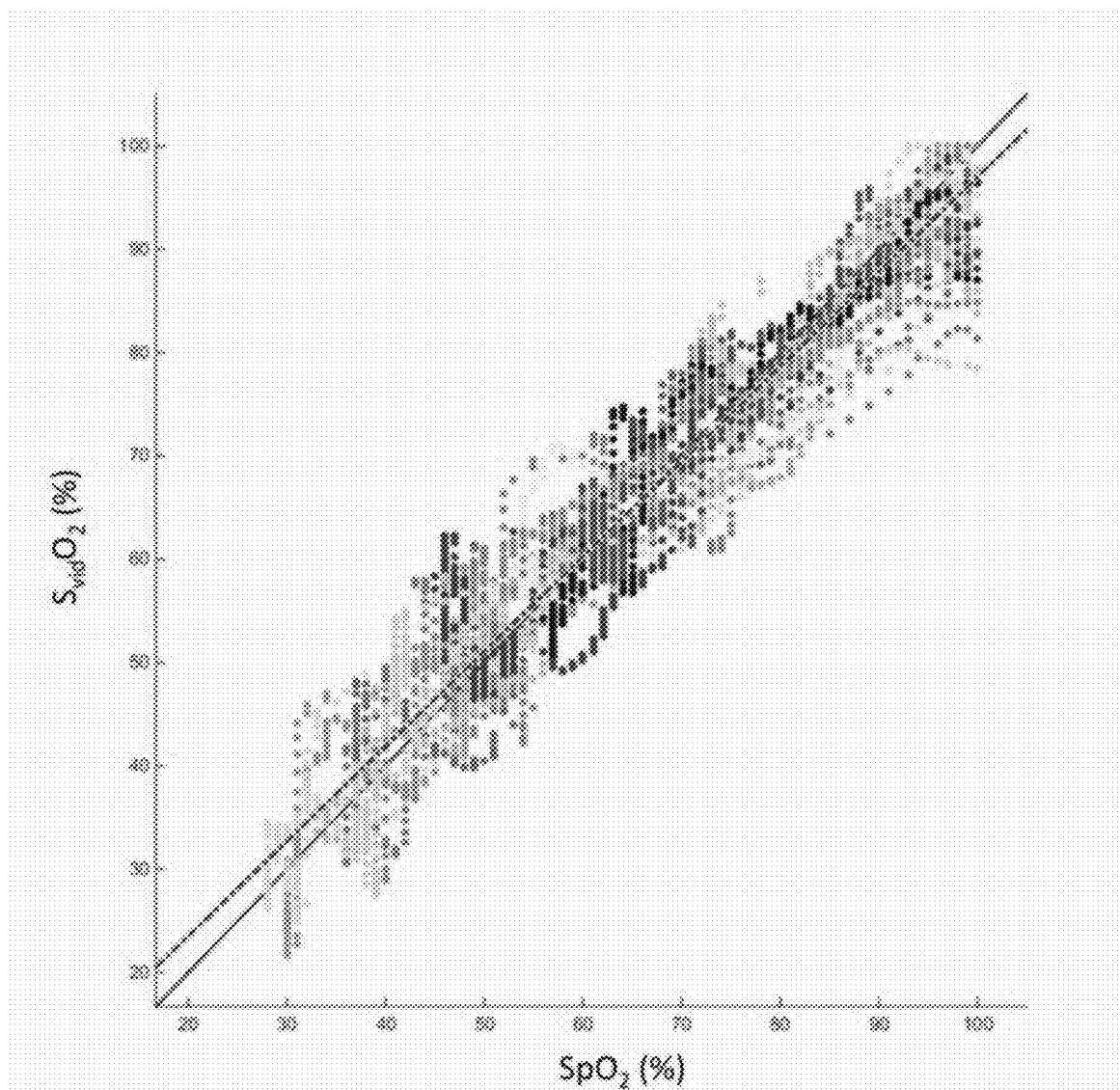
FIG. 21 is a scatter plot of video-based SpO2 measurements against reference SpO2 measurements, according to an embodiment of the invention.

Non-contact video-based monitoring methods have been employed in various test environments to confirm their utility. Some of that testing is summarized below. For example, FIGS. 19, 20, and 21 show video-based measurements of heart rate, respiration rate, and SpO2 as compared to reference measurements, during a clinical study. During the study, the reference measurements were taken as follows: for heart rate and SpO2, from a contact-based pulse oximeter, and for respiration rate, from a ventilator. A video camera was spaced apart from and oriented at the animal subject, and video signals were captured through the course of an oxygen desaturation. The video signals were used to calculate heart rate, respiration rate, and SpO2, and these measurements were compared to the reference measurements, as shown in FIGS. 19, 20, and 21. These figures show good agreement between the video-based measurements and the reference measurements. Two separate regions of interest on the skin were chosen, one for the determination of rates (RRvid and HRvid) and the other for the determination of saturation (SvidO2).

FIG. 19 is a scatter plot of the video-based heart rate measurements on the y-axis, against the reference heart rate measurements on the x-axis (both in beats per minute). The dotted line is a least squares fitted regression line. The expected 1:1 correspondence line is also shown, but is mostly hidden by the regression line, showing very good fit between the two. Each desaturation episode is shaded separately.

FIG. 20 is a scatter plot of the video-based respiration rate measurements against the reference respiratory rate measurements from the ventilator (both in breaths per minute). The dotted line is a least squares fitted regression line. The expected 1:1 correspondence line is shown in solid black. The size of each circle corresponds to the number of data points at that location; this visualization was required due to many co-located data points in the plot.

FIG. 21 is a scatter plot of the video-based SpO2 measurements against the reference SpO2 measurements (both in %). The dotted line is a least squares fitted regression line. The expected 1:1 correspondence line is shown in solid black. Each desaturation episode is shaded separately. Changes in oxygen saturation were calculated using a ratio of ratios derived from the red (R) and green (G) signals, where the two signals were first normalised by dividing their cardiac pulse amplitudes by the signal baseline values. As discussed above, using a standard RGB camera only allows for a relative saturation value to be determined from this normalised ratio of the amplitude of two of the signals. Hence this required calibration against known values from the reference pulse oximeter to provide an absolute value of SvidO2.

The systems and methods described here may be provided in the form of tangible and non-transitory machine-readable medium or media (such as a hard disk drive, hardware memory, etc.) having instructions recorded thereon for execution by a processor or computer. The set of instructions may include various commands that instruct the computer or processor to perform specific operations such as the methods and processes of the various embodiments described here. The set of instructions may be in the form of a software program or application. The computer storage media may include volatile and non-volatile media, and removable and non-removable media, for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic disk storage, or any other hardware medium which may be used to store desired information and that may be accessed by components of the system. Components of the system may communicate with each other via wired or wireless communication. The components may be separate from each other, or various combinations of components may be integrated together into a medical monitor or processor, or contained within a workstation with standard computer hardware (for example, processors, circuitry, logic circuits, memory, and the like). The system may include processing devices such as microprocessors, microcontrollers, integrated circuits, control units, storage media, and other hardware.

Although the present invention has been described and illustrated in respect to exemplary embodiments, it is to be understood that it is not to be so limited, since changes and modifications may be made therein which are within the full intended scope of this invention as hereinafter claimed.

What is claimed is:

1. A video-based method of measuring a patient's vital sign, comprising:
   receiving a video signal from a video camera, the video signal having a field of view that includes exposed skin of a patient;
   extracting from the video signal a time-varying color signal for each of a plurality of regions, each region including exposed skin of the patient;
   identifying a frequency content of each color signal;
   selecting two or more non-adjacent, non-overlapping regions that have a shared frequency content comprising a modulation at a shared frequency;
   combining the color signals of the selected regions;
   measuring a vital sign from the combined color signal; and
   outputting the vital sign for further processing or display.

2. The method of claim 1, wherein combining comprises averaging the color signals from the selected regions.

3. The method of claim 2, wherein the selected regions have different sizes.

4. The method of claim 1, wherein the vital sign comprises heart rate.

5. The method of claim 4, wherein measuring the heart rate comprises accumulating frequency peaks from the combined signal, selecting a median frequency, and updating a running average heart rate from the selected frequency.

6. The method of claim 3, further comprising updating the selected regions by adding or removing regions from the selected regions based on the frequency content of each region.

7. The method of claim 1, further comprising calculating a statistic of the combined color signal, wherein the statistic comprises an amplitude, a variability, a skew, or a signal to noise ratio.

8. The method of claim 7, wherein combining the color signals comprises applying a weight to each color signal that is being combined, the weight being based on the statistic.

9. The method of claim 7, further comprising determining a weight for the vital sign, the weight being based on the statistic, and adding the vital sign to a running average based on the weight.

10. The method of claim 2, wherein selecting the two or more non-adjacent, non-overlapping regions further comprises selecting regions that satisfy a quality criterion, and wherein the quality criterion comprises a signal to noise ratio that satisfies a threshold, or a skew value that satisfies a threshold.

11. The method of claim 10, further comprising removing a color signal from the combined color signal upon failure of the removed color signal to satisfy the criterion.

12. The method of claim 1, wherein extracting the time-varying color signal comprises extracting two time-varying color signals for each region, and wherein measuring the vital sign comprises measuring oxygen saturation from the two time-varying color signals.

13. A camera-based method of measuring a patient's vital sign, comprising:
   receiving an image signal from a camera having a field of view encompassing exposed skin of a patient, the image signal comprising a sequence of image frames over time;
   within the field of view, identifying a plurality of regions;
   for each region of the plurality, extracting an intensity signal comprising a time-varying light intensity detected in the region;
   selecting regions whose intensity signals comprise a modulation at a shared frequency, wherein the selected regions are non-adjacent and non-overlapping in the image frame;
   combining the intensity signals of the selected regions to produce a combined intensity signal; and
   measuring heart rate of the patient from the combined intensity signal.

14. The method of claim 13, wherein the measured vital sign is a first measured vital sign, and wherein the method further comprises:
   selecting a second set of regions whose intensity signals comprise a second modulation at a second, different, shared frequency, wherein the second set of selected regions are non-adjacent in the image frame;
   combining the intensity signals of the second set of selected regions to produce a second combined intensity signal; and
   measuring respiration rate of the patient from the second combined intensity signal.

15. The method of claim 14, further comprising displaying the image signal on a display, highlighting on the display the selected regions for the first vital sign, and highlighting on the display the second, different set of selected regions for the second vital sign.

16. The method of claim 13, wherein the modulation at the shared frequency is above an amplitude threshold.

17. The method of claim 13, wherein extracting the intensity signal for each region comprises extracting a red intensity signal comprising a time-varying average of red values in the region, a green intensity signal comprising a time-varying average of green values in the region, and a blue intensity signal comprising a time-varying average of blue values in the region.

18. A camera-based method of measuring a patient's vital sign, comprising:

receiving an image signal from a camera having a field of view encompassing exposed skin of a patient;

receiving a user input identifying a region in the image signal;

measuring a first vital sign of the patient, comprising:
   from the region, selecting a first set of pixels that exhibit a first modulation at a first shared frequency, wherein the first selected pixels are non-contiguous and non-overlapping; and
   measuring the first vital sign of the patient from the selected first pixels; and outputting the first measured vital sign for further processing or display.

19. The method of claim 18, further comprising:

measuring and outputting a second vital sign of the patient, comprising:
   from the region, selecting a second set of pixels that exhibit a second modulation at a second shared frequency different from the first shared frequency, wherein the second selected pixels are non-contiguous;
   measuring the second vital sign of the patient from the selected second pixels.

20. The method of claim 19, wherein the first vital sign comprises heart rate and the second vital sign comprises respiration rate.

21. The method of claim 18, further comprising receiving a second user input moving the region to a new location, and subsequently measuring the first vital sign from the new location.

22. The method of claim 18, further comprising displaying a number derived from the first measured vital sign, and triggering an alarm based on the displayed number and stored alarm conditions, wherein the stored alarm conditions omit a sensor-off or sensor-disconnect alarm.

* * * * *